US010504624B2

(12) United States Patent
Gurcan et al.

(10) Patent No.: US 10,504,624 B2
(45) Date of Patent: Dec. 10, 2019

(54) SYSTEM AND METHOD FOR SEGMENTATION AND AUTOMATED MEASUREMENT OF CHRONIC WOUND IMAGES

(71) Applicant: Ohio State Innovation Foundation, Columbus, OH (US)

(72) Inventors: Metin N. Gurcan, Dublin, OH (US); Chandan K. Sen, Upper Arlington, OH (US); Gayle Gordillo, Upper Arlington, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 0 days.

(21) Appl. No.: 15/949,657

(22) Filed: Apr. 10, 2018

(65) Prior Publication Data

US 2018/0226154 A1 Aug. 9, 2018

Related U.S. Application Data

(63) Continuation of application No. 15/078,313, filed on Mar. 23, 2016, now Pat. No. 9,990,472.

(Continued)

(51) Int. Cl.
*G06K 9/00* (2006.01)
*G16H 50/20* (2018.01)
(Continued)

(52) U.S. Cl.
CPC ........... *G16H 50/20* (2018.01); *G06F 19/321* (2013.01); *G06K 9/6284* (2013.01); *G06T 7/0016* (2013.01); *G06T 7/62* (2017.01); *G16H 30/20* (2018.01); *G06T 2207/20076* (2013.01); *G06T 2207/30088* (2013.01)

(58) Field of Classification Search
None
See application file for complete search history.

(56) References Cited

U.S. PATENT DOCUMENTS 8,000,777 B2\* 8/2011 Jaeb ..................... A61B 5/0059
382/128
8,276,287 B2\* 10/2012 Estocado ............. A61B 5/1072
33/1 BB (Continued)

OTHER PUBLICATIONS

Veredas et al., "Wound image evaluation with machine learning", Neurocomputing 164 (2015) 112-122, available online Mar. 14, 2015.\*

(Continued)

*Primary Examiner* — Soo Jin Park
(74) *Attorney, Agent, or Firm* — Meunier Carlin & Curfman LLC

(57) ABSTRACT

Disclosed are systems and methods for automated monitoring of the size, area or boundary of chronic wound images. The disclosure includes use of a probability map that measures the likelihood of wound pixels belonging to granulation, slough or eschar, which can then be segmented using any standard segmentation techniques. Measurement of the wound size, area or boundary occurs automatically and without user input related to outlining, filling in, or making measurement lines over the image on a display.

28 Claims, 16 Drawing Sheets
(11 of 16 Drawing Sheet(s) Filed in Color)

Related U.S. Application Data

(60) Provisional application No. 62/136,697, filed on Mar. 23, 2015.

(51) Int. Cl.
*G06K 9/62* (2006.01)
*G06F 19/00* (2018.01)
*G06T 7/00* (2017.01)
*G06T 7/62* (2017.01)
*G16H 30/20* (2018.01)

(56) References Cited

U.S. PATENT DOCUMENTS

| | | | | |
|---|---|---|---|---|
| 8,505,209 | B2* | 8/2013 | Estocado | A61B 5/1072 33/1 BB |
| 8,588,893 | B2* | 11/2013 | Jaeb | A61B 5/0059 382/128 |
| 9,161,716 | B2* | 10/2015 | Estocado | A61B 5/441 |
| 2001/0049609 | A1 | 12/2001 | Girouard et al. | |
| 2010/0111387 | A1* | 5/2010 | Christiansen, II | A61B 5/0059 382/128 |
| 2013/0170718 | A1* | 7/2013 | Ryu | G06K 9/48 382/128 |
| 2013/0179288 | A1* | 7/2013 | Moses | G06Q 10/00 705/26.1 |
| 2013/0331708 | A1 | 12/2013 | Estocado | |
| 2015/0119721 | A1* | 4/2015 | Pedersen | A61B 5/445 600/476 |
| 2015/0150457 | A1* | 6/2015 | Wu | A61B 5/0073 600/425 |
| 2016/0157725 | A1* | 6/2016 | Munoz | A61B 5/0077 600/430 |
| 2017/0076446 | A1* | 3/2017 | Pedersen | G06T 7/0012 |
| 2018/0028108 | A1* | 2/2018 | Shluzas | A61B 5/445 |

OTHER PUBLICATIONS

Callieri et al., "Derma: monitoring the evolution of skin lesions with a 3D system", VMV 2003.*
Casas et al., "Imaging technologies applied to chronic wounds", ISABEL '11, Oct. 26-29.*
Wannous et al., "Fusion of multi-view tissue classification based on wound 3D model", ACIVS 2008, LNCS vol. 5259.*
Burns et al., Development of a Wound Assessment System for Quantitative Chronic Wound Monitoring, p. 7-8, 2002.
Cukjati et al., Measures of wound healing rate, Proceedings of the 22nd Annual EMBS International Conference, Jul. 23-28, 2000, p. 765-768.
Filko et al., WIT A—Application for Wound Analysis and Management, 2010.
Hani et al., Haemoglobin Distribution in Ulcers for Healing Assessment, 2012 4th International Conference on Intelligent and Advanced Systems, 2011.
Hettiarachchi et al., Mobile Based Wound Measurement, p. 298-301, 2013.
Kolesnik et al., Multi-dimensional Color Histograms for Segmentation of Wounds in Images p. 1014-1022, 2005.
Kolesnik et al., Segmentation of Wounds in the Combined Color-Texture Feature Space, Proc. of SPIE vol. 5370:549-556, 2004.
Loizou et al., Evaluation of Wound Healing Process Based on Texture Analysis, Proceedings of the 2012 IEEE 12th International Conference on Bioinformatics & Bioengineering (BIBE), Larnaca, Cyprus, Nov. 11-13, 2012.
Perez et al., Segmentation and Analysis of Leg Ulcers Color Images, p. 262-266, 2001.
Song et al., Automated Wound Identification System Based on Image Segmentation and Artificial Neural Networks, 2012 IEEE International Conference on Bioinformatics and Biomedicine, p. 619-622, 2012.
Veredas et al., Binary Tissue Classification on Wound Images With Neural Networks and Bayesian Classifiers, IEEE Transactions on Medical Imaging vol. 29:410-427, 2010.
Wannous et al., Supervised Tissue Classification from Color Images for a Complete Wound Assessment Tool, Proceedings of the 29th Annual International Conference of the IEEE EMBS Cité Internationale, Lyon, France Aug. 23-26, 2007, p. 6031-6034.
Wantanajittikul et al., Automatic Segmentation and Degree Identification in Burn Color Images, The 2011 Biomedical Engineering International Conference, p. 169-173, 2011.
Weber et al., Remote Wound Monitoring of Chronic Ulcers, IEEE Transactions on Information Technology in Biomedicine vol. 14:371-377, 2010.
FAQ About PictZar Calibrated Digital Meazurements, www.pictzar.com, Mar. 21, 2016.
Contents:PictZar Basics, www.pictzar.com, Mar. 21, 2016.
PictZar Calibrated Digital Meazurements, www.pictzar.com, Mar. 21, 2016.
PictZar Tablet Interface Device Calibrated Digital Meazurements Samsung Windows 8 Tablet PC, www.pictzar.com, Mar. 21, 2016.
Wang et al., "Smartphone-based wound assessment system for patients with diabetes", IEEE Transactions on Biomedical Engineering, vol. 62, issue 2, Feb. 2015.
Mukherjee et al., "Automated tissue classification framework for reproducible chronic wound assessment", Hindawi Publishing Corporation, BioMed Research International, vol. 2014, article ID 851582, 9 pages.
Azevedo-Marques et al., "Segmentation of dermatological ulcers using clustering of color components", CCECE 2013.
Pereira et al., "Classification of dermatological ulcers based on tissue composition and color texture features", ISABEL 2011.
Wannous et al., "Enhanced assessment of the wound-healing process by accurate Multiview tissue classification", IEEE Transactions on Medical Imaging, vol. 30, issue 2, Feb. 2011.
Dorileo et al., "Segmentation and analysis of the tissue composition of dermatological ulcers", CCECE 2010.
Oduncu et al., "Analysis of skin wound images using digital color image processing: a preliminary communication", Int. J. Low Extremity Wounds, vol. 3, No. 3, pp. 151-156, Sep. 2004.

* cited by examiner

FIG. 2B

Patient Dashboard

| Clinic | OSU Wound Center | | | |
|---|---|---|---|---|
| Doctor | Gordillo, G | | | |
| Clinic | ○ East | ⊙ Moorehouse | ○ All | |
| In/out | ⊙ Inpatient | ○ Outpatient | ○ All | |

| | | | | |
|---|---|---|---|---|
| 111345 | Jane Doe | Moorehouse | In | Pressure Ulcer | Stable |
| 111543 | John Smith | Moorehouse | In | Venous Leg Ulcer | Improving |
| 111668 | John Wayne | Moorehouse | In | Diabetic Foot Ulcer | Deteriorating |
| 213884 | Frank Sinatra | Moorehouse | In | Pressure Ulcer | Improving |

FIG. 2E

A First Digital Image Comprising At Least A Portion Of A Wound Is Captured Using An Image Capture Device
302

Determine At Least One Of A Size, Boundary Or An Area Of The Wound
304

Provide The Determined At Least One Of The Size, Boundary Or Area Of The Wound, Wherein The Provided Determined At Least One Of The Size, Area Or Boundary Of The Wound Is Used To Monitor Wound Healing
306

FIG. 3

SYSTEM AND METHOD FOR SEGMENTATION AND AUTOMATED MEASUREMENT OF CHRONIC WOUND IMAGES

CROSS-REFERENCE TO RELATED APPLICATION

This application is a continuation application of U.S. application Ser. No. 15/078,313 filed Mar. 23, 2016, which claims priority to and benefit of U.S. Provisional Patent Application Ser. No. 62/136,697, filed Mar. 23, 2015, both of which are fully incorporated by reference and made a part hereof.

BACKGROUND

A chronic wound, as defined by Centers for Medicare and Medicaid Services, is a wound that has not healed in 30 days. An estimated 6.5 million patients in the United States are affected by chronic wounds, and it is claimed that an excess of US$25 billion is spent annually on treatment of chronic wounds. The burden is growing rapidly due to increasing health care costs, an aging population and a sharp rise in the incidence of diabetes and obesity worldwide. The current state of the art approach in measuring wound size using digital images, known as digital planimetry, requires the clinician to identify wound borders and wound tissue type within the image. This is a time-intensive process and is a barrier to achieving clinical quality benchmarks.

Although wound segmentation from photographic images has been the subject of several studies, most of the work in this area deals with images that are either acquired under controlled imaging conditions, confined to wound region only, or narrowed to specific types of wounds. Because these restrictions are mostly impractical for clinical conditions, there is a need to develop image segmentation methods that will work with images acquired in regular clinical conditions.

Current works in wound segmentation and monitoring as well as existing software tools are as follows. Wannous et al. compared the mean shift, JSEG and CSC techniques in segmenting 25 wound images, before extracting color and textural features to classify the tissues into granulation, slough and necrosis using an SVM classifier. The wound images were taken with respect to a specific protocol integrating several points of views for each single wound, which includes using a ring flash with specific control and placing a calibrated Macbeth color checker pattern near the wounds. They reported that both segmentation and classification work better on granulation than slough and necrosis. Hettiarachchi et al. attempted wound segmentation and measurement in a mobile setting. The segmentation is based on active contour models which identifies the wound border irrespective of coloration and shape. The active contour process was modified by changing the energy calculation to minimize points sticking together as well as including pre-processing techniques to reduce errors from artifacts and lighting conditions. Although the accuracy was reported to be 90%, the method is rather sensitive to camera distance, angle and lighting conditions.

In a work by Veredas et al., a hybrid approach based on neural networks and Bayesian classifiers is proposed in the design of a computational system for tissue identification and labeling in wound images. Mean shift and region-growing strategy are implemented for region segmentation. The neural network and Bayesian classifiers are then used to categorize the tissue based on color and texture features extracted from the segmented regions, with 78.7% sensitivity, 94.7% specificity and 91.5% accuracy reported. Hani et al. presented an approach based on utilizing hemoglobin content in chronic ulcers as an image marker to detect the growth of granulation tissue. Independent Component Analysis is employed to extract grey level hemoglobin images from Red-Green-Blue (RGB) color images of chronic ulcers. Data clustering techniques are then implemented to classify and segment detected regions of granulation tissue from the extracted hemoglobin images. 88.2% sensitivity and 98.8% specificity were reported on a database of 30 images.

Perez et al. proposed a method for the segmentation and analysis of leg ulcer tissues in color images. The segmentation is obtained through analysis of the red, green, blue, saturation and intensity channels of the image. The algorithm, however, requires the user to provide samples of the wound and the background before the segmentation can be carried out. Wantanajittikul et al. employs the Cr-transformation, Luv-transformation and fuzzy c-means clustering technique to separate the burn wound area from healthy skin before applying mathematical morphology to reduce segmentation errors. To identify the degree of the burns, h-transformation and texture analysis are used to extract feature vectors for SVM classification. Positive predictive value and sensitivity between 72.0% and 98.0% were reported in segmenting burn areas in five images, with 75.0% classification accuracy.

Song and Sacan proposed a system capable of automatic image segmentation and wound region identification. Several commonly used segmentation methods (k-means clustering, edge detection, thresholding, and region growing) are utilized to obtain a collection of candidate wound regions. Multi-Layer Perceptron (MLP) and Radial Basis Function (RBF) are then applied with supervised learning in the prediction procedure for the wound identification. Experiments on 92 images from 14 patients (78 training, 14 testing) showed that both MLP and RBF have decent efficiency, with their own advantages and disadvantages. Kolesnik and Fexa used color and textural features from 3-D color histogram, local binary pattern and local contrast variation with the support vector machine (SVM) classifier to segment 23 wound images based on 50 manually segmented training images. The SVM generated wound boundary is further refined using deformable snake adjustment. Although this study does not have the aforementioned restrictions (i.e. acquired under controlled imaging conditions, confined to wound region only, or narrowed to specific types of wounds), results were reported on a relatively small set of images. An average error rate of 6.6%, 22.2% and 5.8% were reported for the color, texture and hybrid features, respectively.

In addition to wound segmentation, wound healing and monitoring have been the subject of several studies on wound image analysis. Cukjati et al. presented their findings on how the wound-healing rate should be defined to enable appropriate description of wound healing dynamics. They suggested that wound area measurements should be transformed to percentage of initial wound area and fitted to a delayed exponential model. In the suggested model, the wound healing rate is described by the slope of the curve is fitted to the normalized wound area measurements over time after initialization delay. Loizou et al. established a standardized and objective technique to assess the progress of wound healing in a foot. They concluded that while none of the geometrical features (area, perimeter, x-, y-coordinate)

show significant changes between visits, several texture features (mean, contrast, entropy, SSV, sum variance, sum average) do, indicating these features might provide a better wound healing rate indication. Finally, Burns et al. evaluated several methods for quantitative wound assessment on diabetic foot ulcers, namely wound volume, wound area, and wound coloration.

There are also quite a few software tools for wound analysis and monitoring currently available. All the software, however, has yet to incorporate automated or semi-automated wound detection or segmentation so that the clinician's initial involvement can be minimized. For example, PictZar™ Digital Planimetry Software (PictZar.com, Elmwood Park, N.J.) is commercial software for wound analysis which provides measurements such as length, width, surface area, circumference, and estimated volume to the users. The software, however, does not incorporate automated or semi-automated wound detection; instead it requires user drawings and calibration for the above measurements to be computed. Filko et al. developed WITA, a color image processing software application that has the capability to analyze digital wound images, and based on learned tissue samples, the program classifies the tissue and monitors wound healing. The wound tissue types are divided into black necrotic eschar, yellow fibrin or slough, red granulation tissue and unclassified parts of the image, although no evaluation against the known ground truth was presented for the image analysis part of the software. To obtain wound dimensions, users must mark the distance on the photograph that is equivalent to 1 cm (or 1 inch). A different approach to wound monitoring software and hardware was proposed by Weber et al. They developed a new "wound mapping" device, which is based on electrical impedance spectroscopy and involves the multi-frequency characterization of the electrical properties of wound tissue under an electrode array. This approach, however, requires major changes to the daily clinical routine in wound care.

Therefore, systems and methods are desired that overcome challenges in the art, some of which are described above. There is a need for a timely and accurate method to document the size and evolving nature of chronic wounds in both the inpatient and outpatient settings. Such an application can potentially reduce clinicians' workload considerably; make the treatment and care more consistent and accurate; increase the quality of documentation in the medical record and enable clinicians to achieve quality benchmarks for wound care as determined by the Center for Medicare Services.

SUMMARY

A wound exhibits a complex structure and may contain many types of tissue such as granulation, slough, eschar, epithelialization, bone, tendon and blood vessels, each with different color and texture characteristics. Disclosed herein are systems and methods that use a probability map that measures the likelihood of wound pixels belonging to granulation, slough or eschar, which can then be segmented using any standard segmentation techniques. As described herein, granulation, slough and eschar tissues as these are the three most commonly seen tissues in wounds.

Disclosed herein are methods for automated segmentation and measurement of chronic wound images. The method may comprise obtaining a digital image, wherein at least a portion of the image comprises a wound. At least one of a size, a boundary or an area of the wound is determined. This is performed automatically and without a user outlining, filling in, or making lines over the image on a display. The determined at least one of the boundary, the size or the area of the wound is reported and can be used to monitor wound healing.

A method for automated segmentation and measurement of temporal changes in chronic wound images is disclosed. The method may comprise obtaining a first digital image, wherein at least a portion of the first digital image comprises a wound; automatically, and with or without user input, determining at least one of a first boundary, a first size, or a first area of the wound at the first time by classifying one or more pixels of the first digital image as belonging to the wound or not being associated with the wound; obtaining a second digital image of the at least the portion of the wound, wherein the second digital image is captured at a time that is after the first digital image was captured; automatically determining, and with or without user input, at least one of a second boundary, a second size, or a second area of the wound at the second time by classifying one or more pixels of the second digital image as belonging to the wound or not being associated with the wound; comparing the determined at least one of the first boundary, first size or first area of the wound to the determined at least one of the second boundary, second size or the second area of the wound to determine if the at least one of the boundary, size or the area of the wound is changing by getting smaller or getting larger, or if it is staying the same; and providing the results of the comparison, wherein the provided comparison is used to monitor wound healing.

Also disclosed herein are systems for segmentation and automated measurement of chronic wound images. The system may comprise an image capture device; a memory; and a processor in communication with the memory, wherein the processor executes computer-readable instructions stored in the memory that cause the processor to obtain a digital image that has been captured by the image capture device, wherein at least a portion of the image comprises a wound; automatically determine at least one of a size, boundary or an area of the wound; and provide the determined at least one of the boundary, the size or the area of the wound, wherein the provided determined at least one of the size or the area of the wound is used to monitor wound healing.

Additional advantages will be set forth in part in the description which follows or may be learned by practice. The advantages will be realized and attained by means of the elements and combinations particularly pointed out in the appended claims. It is to be understood that both the foregoing general description and the following detailed description are exemplary and explanatory only and are not restrictive, as claimed.

BRIEF DESCRIPTION OF THE DRAWINGS

The accompanying drawings, which are incorporated in and constitute a part of this specification, illustrate embodiments and together with the description, serve to explain the principles of the methods and systems. The patent or application file contains at least one drawing executed in color. Copies of this patent or patent application publication with color drawing(s) will be provided by the Office upon request and payment of the necessary fee:

FIG. 2B is an image of an exemplary graphic display of wound assessment software that shows the original digital image of the wound, the boundary of the wound as an overlay over the original digital image of the wound, and the determined size (in centimeters) and area (in square-centimeters), as automatically calculated by the software;

FIGS. 2D and 2E are exemplary images of generated reports for monitoring wound treatment and healing and/or dashboards for quick assessments of multiple patients, respectively;

FIG. 3 is a flowchart that illustrates an exemplary method of for making segmentation and automated measurements of chronic wound images;

FIG. 9A shows the transformation of S and V using Eq. 2 and Eq. 3, while

DETAILED DESCRIPTION

Figure 1A:
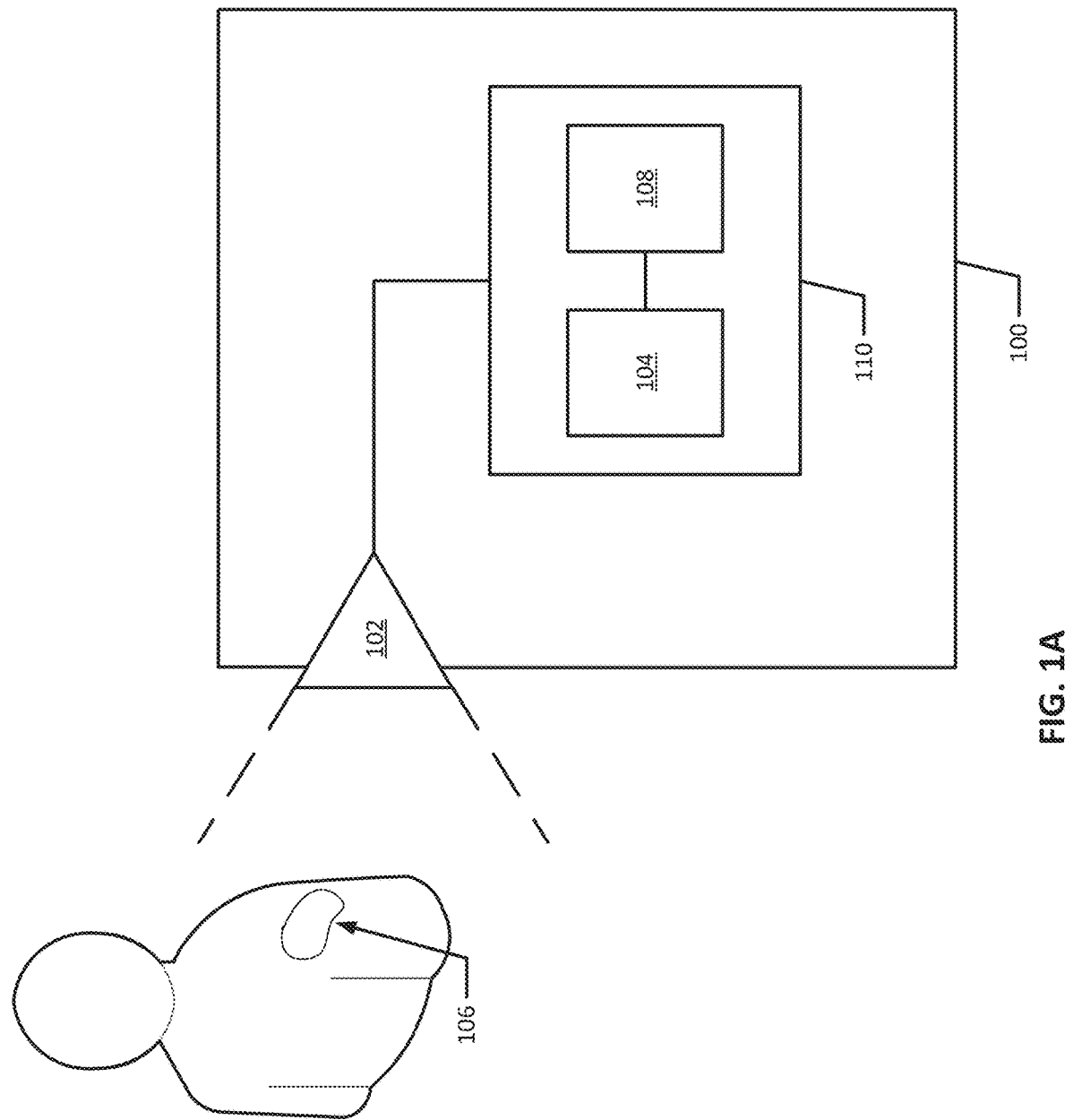
FIG. 1A illustrates an exemplary overview apparatus for making segmentation and automated measurements of chronic wound images.

Before the present methods and systems are disclosed and described, it is to be understood that the methods and systems are not limited to specific synthetic methods, specific components, or to particular compositions. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

As will be appreciated by one skilled in the art, the methods and systems may take the form of an entirely hardware embodiment, an entirely software embodiment, or an embodiment combining software and hardware aspects. Furthermore, the methods and systems may take the form of a computer program product on a computer-readable storage medium having computer-readable program instructions (e.g., computer software) embodied in the storage medium. More particularly, the present methods and systems may take the form of web-implemented computer software. Any suitable computer-readable storage medium may be utilized including hard disks, CD-ROMs, optical storage devices, or magnetic storage devices.

Embodiments of the methods and systems are described below with reference to block diagrams and flowchart illustrations of methods, systems, apparatuses and computer program products. It will be understood that each block of the block diagrams and flowchart illustrations, and combinations of blocks in the block diagrams and flowchart illustrations, respectively, can be implemented by computer program instructions. These computer program instructions may be loaded onto a general purpose computer, special purpose computer, or other programmable data processing apparatus to produce a machine, such that the instructions which execute on the computer or other programmable data processing apparatus create a means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including computer-readable instructions for implementing the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the flowchart block or blocks.

Accordingly, blocks of the block diagrams and flowchart illustrations support combinations of means for performing the specified functions, combinations of steps for performing the specified functions and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions or steps, or combinations of special purpose hardware and computer instructions.

The present methods and systems may be understood more readily by reference to the following detailed description of preferred embodiments and the Examples included therein and to the Figures and their previous and following description.

FIG. 1 illustrates an exemplary overview apparatus for making segmentation and automated measurement of chronic wound images. As shown in FIG. 1, one embodiment of the apparatus 100 comprises an image capture mechanism 102. In one aspect, the image capture mechanism 102 can be a camera. The image capture mechanism 102 can take still and/or video images. Generally, the image capture mechanism 102 will be a digital camera, but can be an analog device equipped with or in communication with an appropriate analog/digital converter. The image capture mechanism 102 may also be a webcam, scanner, recorder, or any other device capable of capturing a still image or a video.

As shown in FIG. 1A, the image capture mechanism 102 is in direct communication with a computing device 110 through, for example, a network (wired (including fiber optic)), wireless or a combination of wired and wireless) or a direct-connect cable (e.g., using a universal serial bus (USB) connection, IEEE 1394 "Firewire" connections, and the like). In other aspects, the image capture mechanism 102 can be located remotely from the computing device 110, but capable of capturing an image and storing it on a memory device such that the image can be downloaded or transferred to the computing device 110 using, for example, a portable memory device and the like. In one aspect, the computing device 110 and the image capture mechanism 102 can comprise or be a part of a device such as a smart device, smart phone, tablet, laptop computer or any other fixed or mobile computing device.

In a basic configuration, the computing device 110 can be comprised of a processor 104 and a memory 108. The processor 104 can execute computer-readable instructions that are stored in the memory 108. Moreover, images captured by the image capture device 102, whether still images or video, can be stored in the memory 108 and processed by the processor 104 using computer-readable instructions stored in the memory 108.

The processor 104 is in communication with the image capture device 102 and the memory 108. The processor 104 can execute computer-readable instructions stored on the memory 108 to capture, using the image capture device 102, an image. In one aspect, the captured image can include a wound 106 of a subject. The wound 106 may be a chronic wound.

Figure 1B:
FIG. 1B is an example of a photograph of a wound having a label of known size proximate to the wound, which can be used to determine pixel size.

The processor 104 can further execute computer-readable instructions stored on the memory 108 to capture, using the image capture device 102, a first digital image wherein at least a portion of the first image comprises a wound. The processor can execute computer-readable instructions to automatically determine at least one of a size, boundary or an area of the wound and provide the determined at least one of the boundary, size or area of the wound, wherein the provided determined at least one of the size or the area of the wound is used to monitor wound healing. The processor determined the at least one of the size, boundary or the area of the wound automatically—there is no user input required to outline, fill in, or make measurement lines over the image on a display. Though not required, in some instances where a label or index card is used as the object of known size, it may have thereon identification or other information about the subject, which can be used to verify that the image is of the proper subject. For example, FIG. 1B is an example of a photograph of a wound having a label of known size proximate to the wound, which can be used to determine pixel size. In FIG. 1B, descriptive information about the subject is obscured to protect the subject's privacy.

When determining at least one of the size, boundary or the area of the wound, the computer-readable instructions can cause the processor to automatically classify one or more pixels of the digital image as belonging to the wound or not being associated with the wound. In one aspect, the processor executed computer-readable instructions to determine a pixel size for at least the one or more pixels of the digital image. For example, in one instance an object having a known size is placed proximate to the wound and the digital image captures at least a portion of the wound and the object having a known size. The object of known size can be, for example, a ruler, an index card, a label with a known size, or any other material or object in which the size is known or can be measured. Though not required, in some instances where a label or index card is used as the object of known size, it may conveniently have thereon identification or other information about the subject which can be used to verify that the image is of the proper subject or other descriptive information.

The processor can execute computer readable instructions that determine the pixel size by detecting the label in the digital image using one or more image analysis algorithms such as color region filtering, measurement of rectangularity, and the like; measuring a number of pixels that span a given detected edge of known size of the label; and determining the pixel size by dividing the known size of the given detected edge by the number of pixels that span the given detected edge of the label.

Classifying the one or more pixels of the digital image as belonging to the wound or not being associated with the wound comprises the processor executing computer-readable instructions that segment the one or more pixels of the digital image as belonging to the wound based on a color of the at least one or more pixels of the digital image. In various aspects, the processor may execute computer-readable instruction wherein the one or more pixels segmented as belonging to the wound are further identified as granulation, slough or eschar tissues based on a probability of the pixel belonging to a color of a four-dimensional color map. For example, the probability of the pixel belonging to the color of the four-dimensional color map can be computed based on the distance of the image pixels to red, yellow, black and white colors in a modified Hue-Saturation-Value (HSV) color space, though other color spaces are also contemplated (RGB, HSV, CIE L*a*b* etc.). A probability matrix is generated that has the probability of each pixel examined being the identified colors. Pixels having the highest probability of being red are associated with granulation tissue, pixels having the highest probability of being yellow are associated with slough tissue, and pixels having the highest probability of being black are associated with eschar tissue. Pixels having the highest probability of being white are associated with epibole tissue, skin or the object of a known size in the digital image used to determine pixel size. In one example, the one or more pixels segmented as belonging to the wound are further identified as granulation, slough or eschar tissue based on the probability of the pixel belonging to the color of a four-dimensional color map as determined by a region-growing algorithm or an optimal thresholding algorithm, though other algorithms are also contemplated.

Figure 1C:
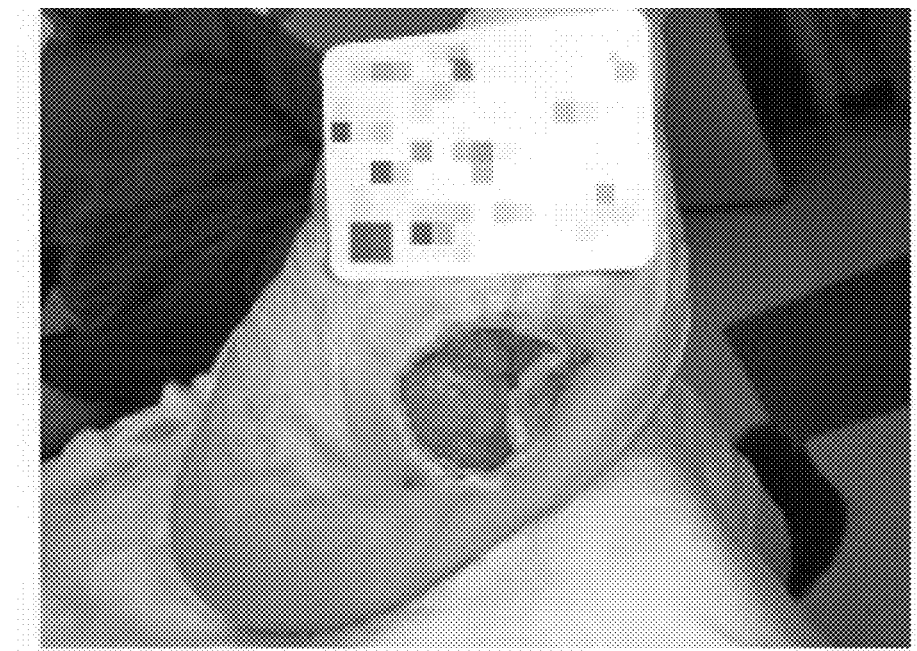
FIG. 1C is a photograph of a wound wherein the processor executing computer-readable instructions has determined a boundary of the wound, and the boundary is shown as an overlay over the image of the wound, with the boundary being a different color (in this case, green)

The processor can further execute computer-readable instructions to outline the boundary of the wound in the digital image and report the boundary either as a collection of x, y coordinates, or as an overlay on the original digital image with a markup—a color drawing or image that can distinguish the boundary from the rest of the wound and surrounding tissue. In one non-limiting example, the processor may execute computer-readable instructions to determine the boundary of the wound and report the wound boundary as an ordered vector of pixel coordinates. For example, as shown in the photograph of FIG. 1C, the processor executing computer-readable instructions has determined a boundary of the wound, and the boundary is shown as an overlay over the image of the wound, with the boundary being a different color (in this case, green).

Figure 2A:
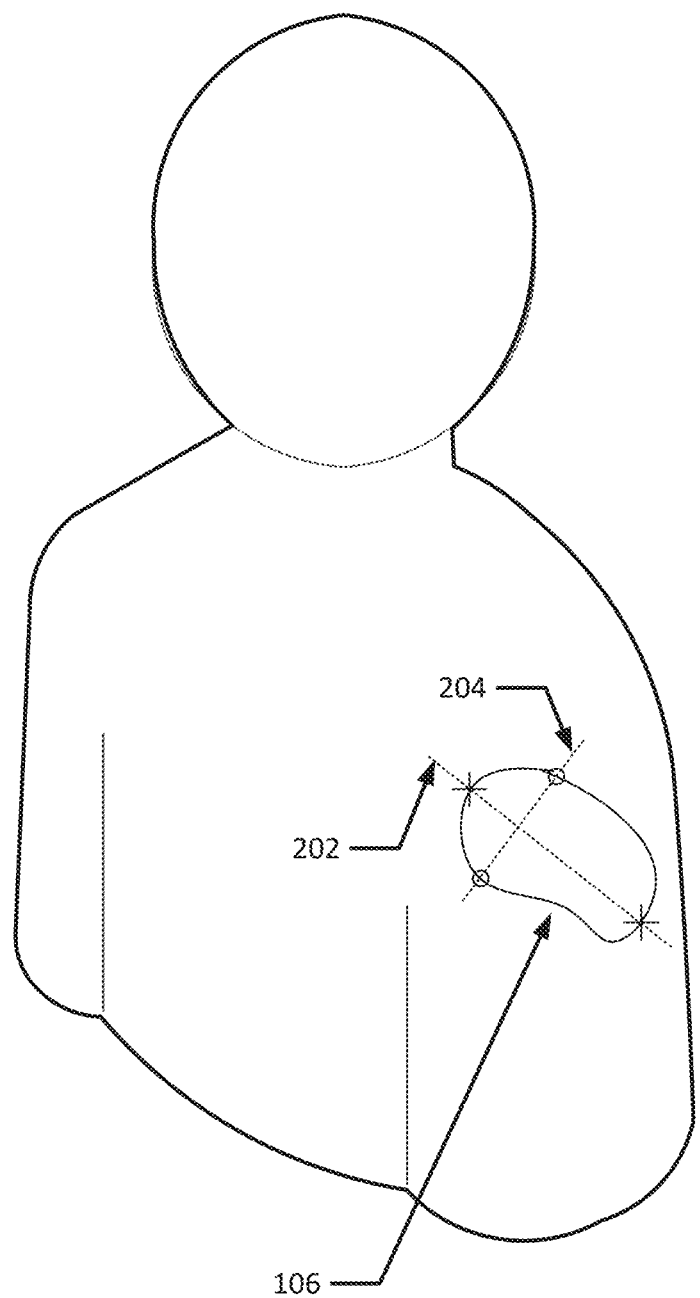
FIG. 2A illustrates a process for determining the size of a wound.
Figure 2B:
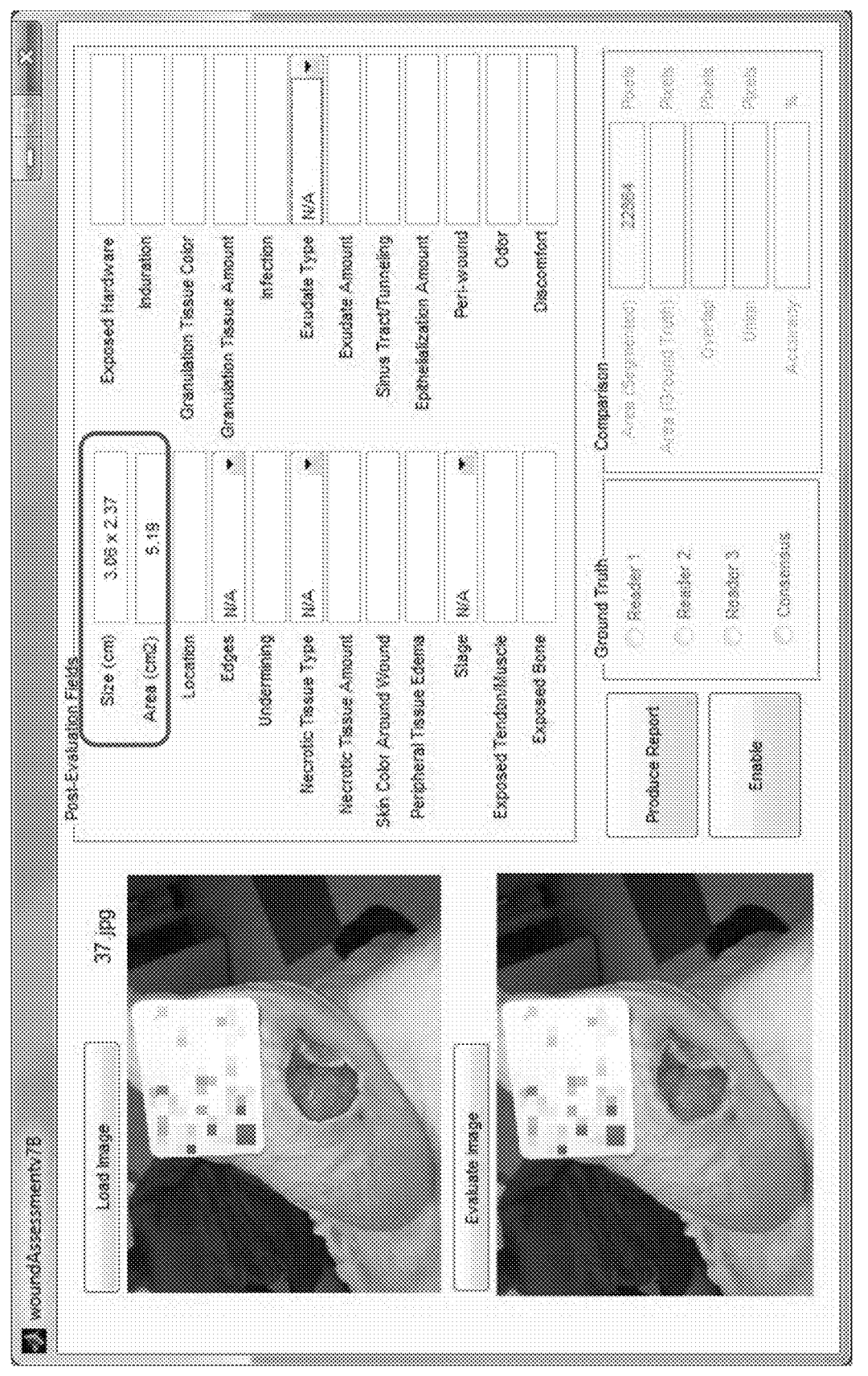

As noted above, the processor can also execute computer-readable instructions to determine the size and area of a wound. One example of determining the size and area of a wound comprises the processor executing computer-executable instructions to determine a maximum distance between two boundary pixel values. For example, an illustrative dashed line 202 is drawn between two wound boundary pixels (illustrated with X's in FIG. 2A) having a maximum distance of separation. The maximum distance between the two boundary pixels is reported as the length of the wound. This distance can be reported as units of measure (e.g., millimeter, centimeters, inches, etc.) or as a number of pixels or in any other relevant units. The processor further executes computer readable instructions to determine a perpendicular maximum distance between two boundary pixels. The perpendicular maximum distance is a maximum distance between two boundary pixels such that a straight line 204 drawn between the two boundary pixels (illustrated with O's in FIG. 2) that form the perpendicular maximum distance would be perpendicular to the straight line 202 drawn between the two boundary pixels that form the length of the wound. The perpendicular maximum distance is reported as a width of the wound. The processor may further execute computer-readable instructions to calculate pixel values of pixels that belong to the wound that are within the boundary of the wound report the total pixel values within the wound boundary as the area of the wound. FIG. 2B is an image of an exemplary graphic display of wound assessment software that shows the original digital image of the wound, the boundary of the wound as an overlay over the original digital image of the wound, and the determined size (in centimeters) and area (in square-centimeters), as automatically calculated by the software.

Furthermore, in various aspects, additional digital images of the wound 106 of the subject can be obtained over time. For each image captured, the processor can execute computer-readable instructions to determine at least one of a size, boundary or an area of the wound, as described herein. The processor can further execute computer-readable instructions to compare the determined at least one of the size or the area of the wound at a first time to the determined at least one of the size or the area of the wound at a second, later time to determine if the at least one of the size or the area of the wound is getting smaller, getting larger, or staying the same. The processor can execute computer-readable instruction to automatically analyze the changes, report how much change since the last visit (for example, wound size, characteristics (e.g. % of tissue composition), etc.). This information can be used in a treatment plan. For example, the wound can be medically treated in accordance with the determination that the at least one of the size or the area of the wound is getting smaller, getting larger, or staying the same. In some instances, the medical decision may comprise "watchful waiting."

Figure 2C:
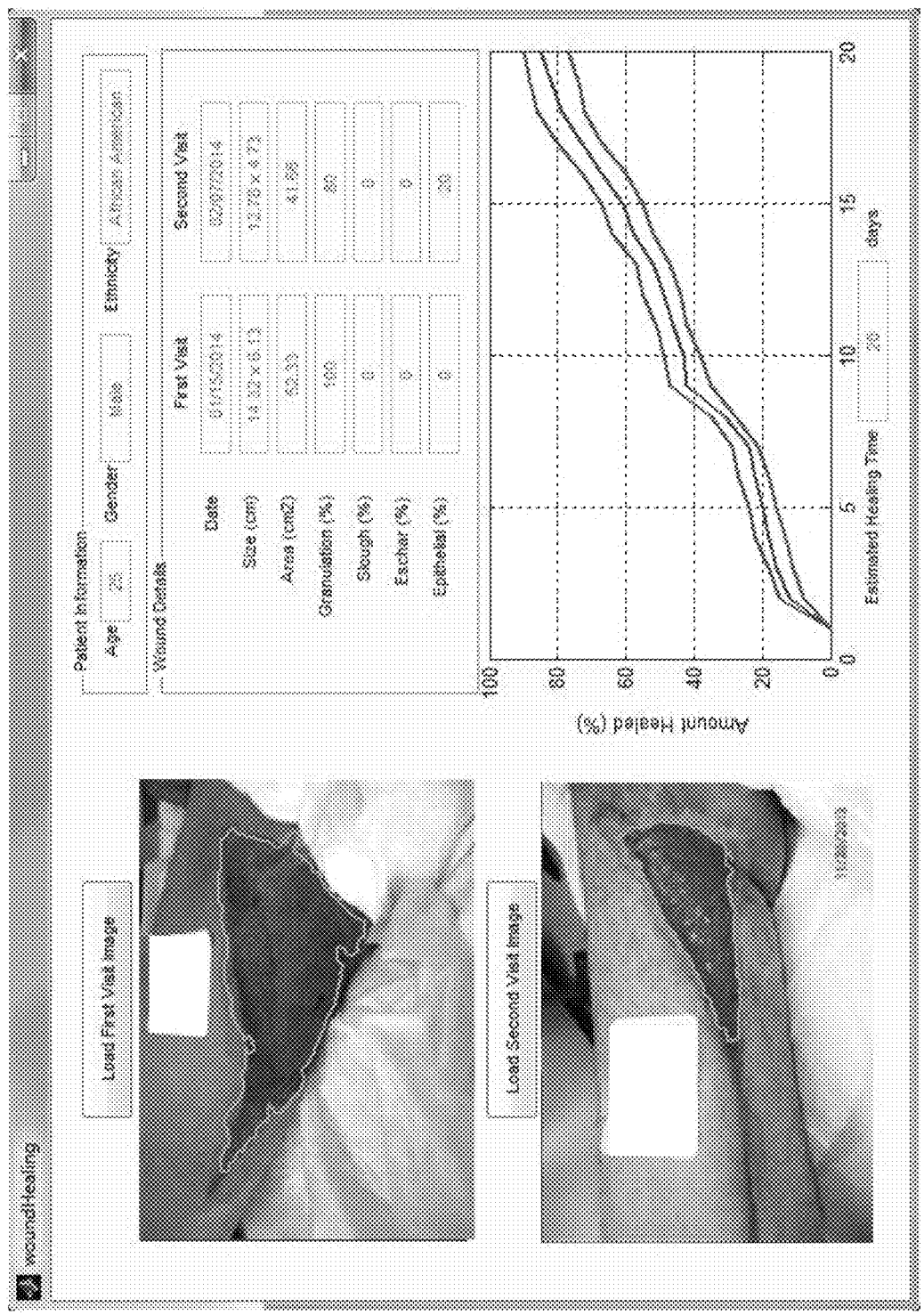
FIG. 2C is an image of an exemplary graphic display of wound assessment software that shows a digital image of a wound captured at a first time, with its boundary, and a second digital image of the same wound captured at a second, later, time (also with its boundary)

In various aspects, the processor can execute computer-readable instructions for predicting at least one timeline for healing of the wound. The predicting of the at least one timeline for healing of the wound can consider demographic (e.g., race, age, gender, etc.) and medical characteristics (diabetic, smoker, etc.) of a patient associated with the wound. The processor can further execute computer-readable instructions for displaying the at least one predicted timeline for healing of the wound. For example, FIG. 2C is an image of an exemplary graphic display of wound assessment software that shows a digital image of a wound captured at a first time, with its boundary, and a second digital image of the same wound captured at a second, later, time (also with its boundary). As can be seen in the "First Visit" and "Second Visit" data displayed in this image, the wound size has decreased in the time elapsed between the first visit and the second visit, as has the wound area. This information can be used to project an estimated healing timeline, as shown in FIG. 2C. In various embodiments, there can be multiple timelines for healing based upon, for example, average healing, faster than average healing, slower than average healing, and the like. This is illustrated in the multiple timelines for healing in FIG. 2C.

Figure 2D:
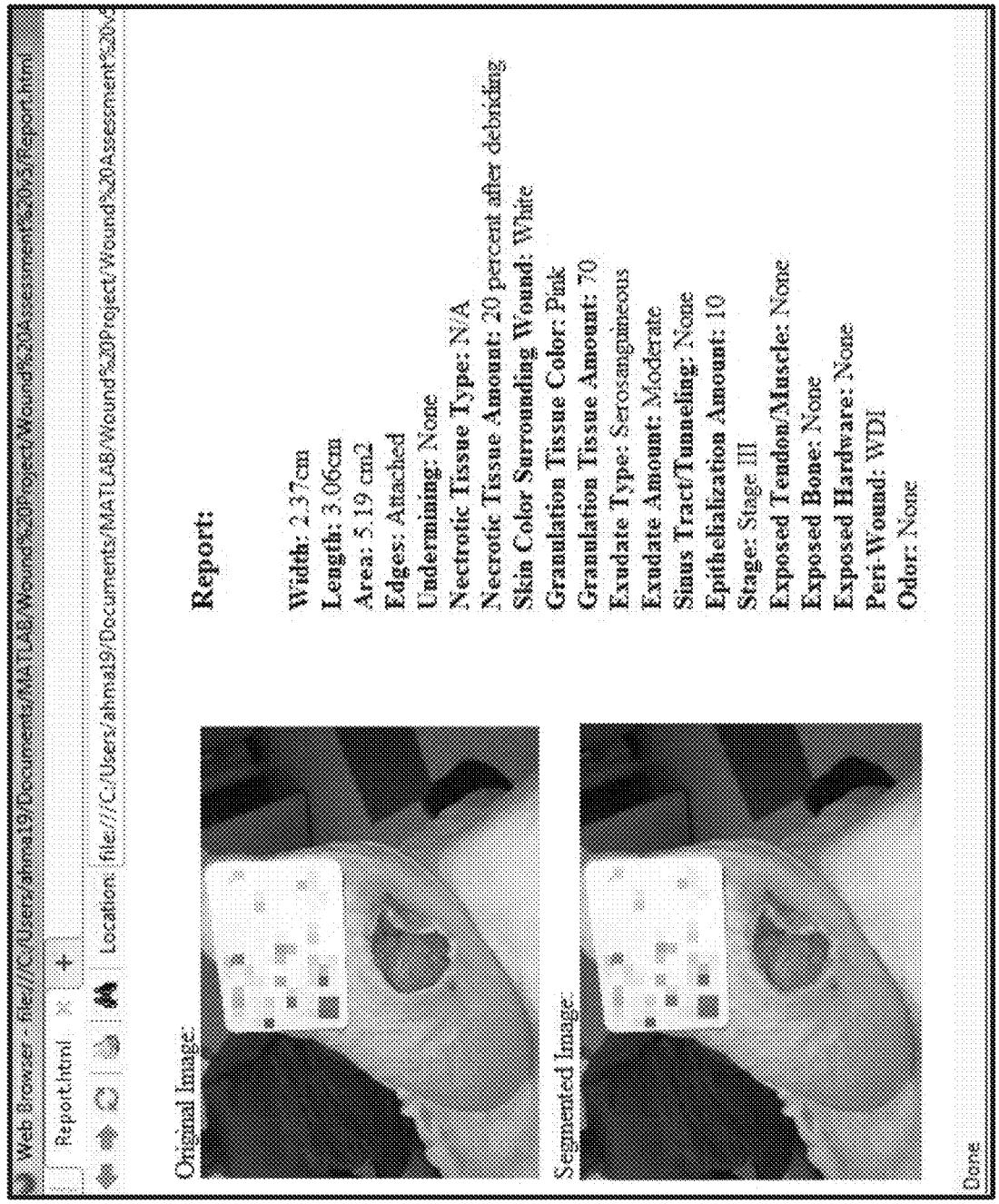

Wound assessment software such as that described herein can also generate reports for monitoring wound treatment and healing and/or dashboards for quick assessments of multiple patients. Exemplary images of such reports and dashboards are shown in FIGS. 2D and 2E, respectively. In various aspects, the processor executing computer-executable instructions can cause various alerts or updates to be sent regarding the wound analysis. For example, an alert can be sent by various means (e.g., phone, pager, text, secure email, and the like). Such alerts can be sent to, for example, medical personnel, the patient, the patient's family, etc.

The system described above and illustrated with reference to FIGS. 1 and 2 may also benefit from adaptive learning. For example, feedback can be provided by experts that evaluation the segmentation of the images and the segmentation and classification parameters can be updated based on the positive and negative feedback FIG. 3 is a flowchart that illustrates an exemplary method of for making segmentation and automated measurements of chronic wound images. In FIG. 3, the exemplary method comprises 302, obtaining a digital image, wherein at least a portion of the image comprises a wound. The digital image may be obtained directly via an image capture device as described herein, or it can be retrieved from the file. For example, a patient could be prompted to take a picture of his or her wound and email, text or otherwise transmit it to their medical professional for analysis. This could occur on a periodic basis.

At 304, at least one of a size, boundary or an area of the wound is determined from the digital image. Generally, this process comprises classifying one or more pixels of the digital image as belonging to the wound or not being associated with the wound. For determining a size or area of the wound, a pixel size is determined for at least the one or more pixels of the digital image that are classified as belonging to the wound. One way of determining pixel size is by placing an object of a known size in the digital image proximate to the wound. Other ways can involve taking the image of the wound at a measured distance from the image capture device, triangulation, etc. If using an object of known size, the object may be a label of known size. Determining the pixel size may comprise detecting the label in the digital image using image analysis algorithms; measuring a number of pixels that span a given detected edge of known size of the label; and determining the pixel size by dividing the known size of the given detected edge by the number of pixels that span the given detected edge of the label. If using a label, it may comprise thereon descriptive information of a patient associated with the wound. Determining the size and area of a wound may comprise determining a maximum distance between two boundary pixel values; reporting the maximum distance as a length of the wound; determining a perpendicular maximum distance between two boundary pixels, wherein the perpendicular maximum distance is a maximum distance between two boundary pixels such that a straight line drawn between the two boundary pixels that form the perpendicular maximum distance would be perpendicular to a straight line drawn between the two boundary pixels that form the length of the wound; reporting the perpendicular maximum distance as a width of the wound; calculating pixel values of pixels that belong to the wound that are within the boundary of the wound; and reporting the total pixel values within the wound boundary as the area of the wound.

Returning to the process of classifying one or more pixels of the digital image as belonging to the wound or not being associated with the wound, this may comprise segmenting the one or more pixels of the digital image as belonging to the wound based on a color of the at least one or more pixels of the digital image. Each of the one or more pixels segmented as belonging to the wound can be further identified as granulation, slough or eschar tissue based on a probability of the pixel belonging to a color of a four-dimensional color map. The probability of the pixel belonging to the color of the four-dimensional color map can be computed based on the distance of the image pixels to red, yellow, black and white colors in a modified Hue-Saturation-Value (HSV) color space. Pixels having the highest probability of being red are associated with granulation tissue, pixels having the highest probability of being yellow are associated with slough tissue, and pixels having the highest probability of being black are associated with eschar tissue. Pixels having the highest probability of being white are associated with epibole tissue, skin or an object of a known size in the digital image used to determine pixel size. The one or more pixels segmented as belonging to the wound can be further identified as granulation, slough or eschar tissue based on the probability of the pixel belonging to the color of a four-dimensional color map as determined by a region-growing algorithm or an optimal thresholding algorithm.

Alternatively or optionally, the exemplary method may further comprise determining the boundary of the wound and reporting the wound boundary as an ordered vector of pixel coordinates. The boundary of the wound may be displayed on the original digital image of the wound as an overlay on the original image with a color that's distinguishable from both the wound and surrounding tissue.

At 306, the determined at least one of the boundary, the size, or the area of the wound is provided, wherein the provided determined at least one of the size or the area of the wound is used to monitor wound healing. For example, the determined at least one of the size or the area of the wound at a first time can be compared to the determined at least one of the size or the area of the wound at a second, later, time to determine if the at least one of the size or the area of the wound is getting smaller, getting larger, or staying the same. The comparison may be reviewed by medical personnel and a course of treatment determined from the comparison. For example, the wound may be medically treated in accordance with the determination that the at least one of the size or the area of the wound is getting smaller, getting larger, or staying the same.

Alternatively or optionally, the exemplary method may further comprise predicting at least one timeline for healing of the wound. Predicting the at least one timeline for healing of the wound may consider the demographic and medical characteristics of a patient associated with the wound. The at least one predicted timeline for healing of the wound may be graphically displayed by computer software.

The system has been described above as comprised of units. One skilled in the art will appreciate that this is a functional description and that the respective functions can be performed by software, hardware, or a combination of software and hardware. A unit can be software, hardware, or a combination of software and hardware. The units can comprise software for discriminating tissue of a specimen. In one exemplary aspect, the units can comprise a computing device that comprises a processor 321 as illustrated in FIG. 4 and described below.

Figure 4:
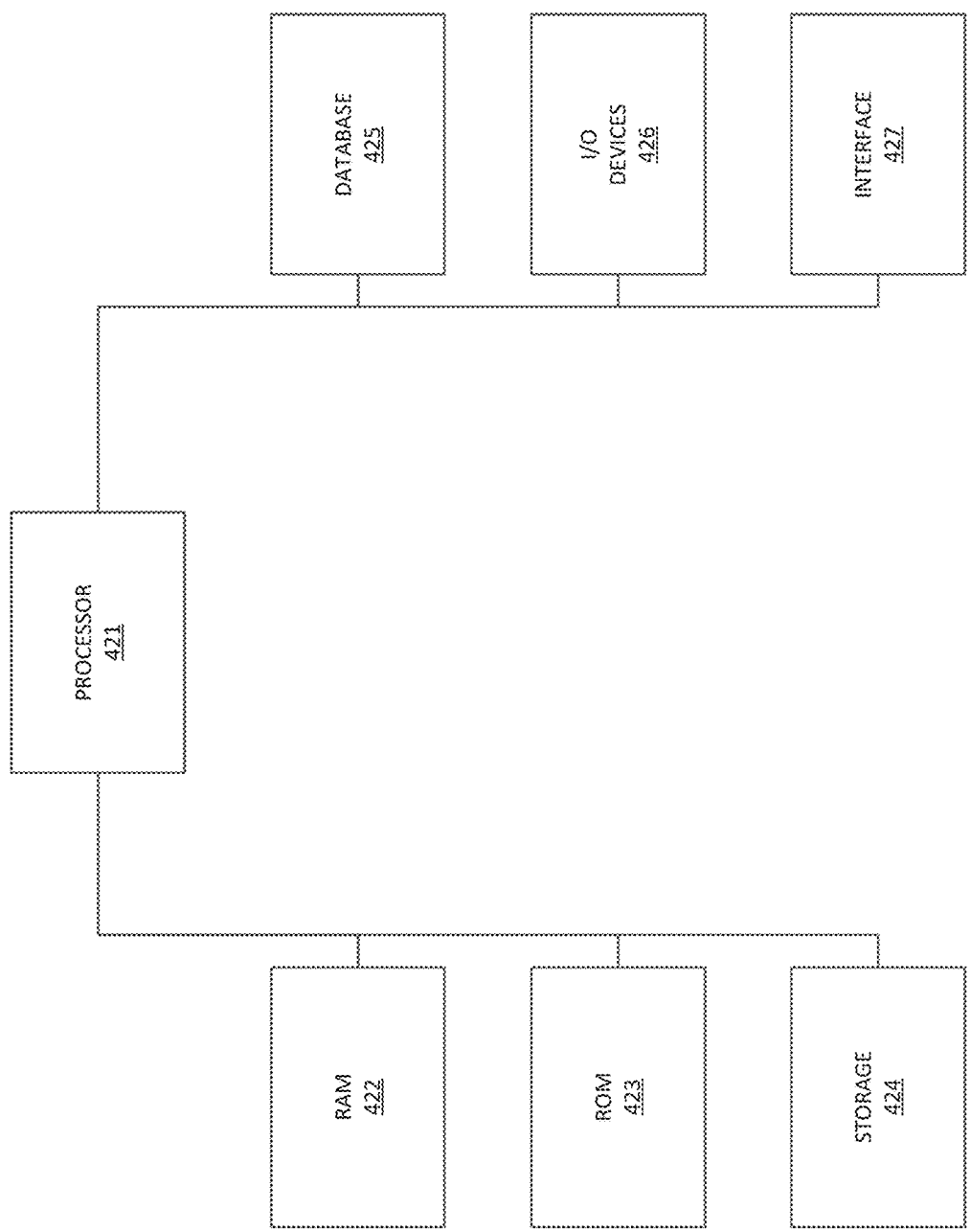
FIG. 4 illustrates an exemplary computer that can be used for making segmentation and automated measurements of chronic wound images.
Figure 5C:
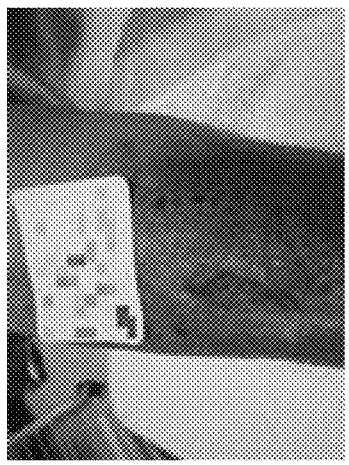
FIGS. 5A, 5B, 5C and 5D illustrate images with complicated backgrounds, especially those red, yellow and black objects, that may interfere with the segmentation process.
Figure 5B:
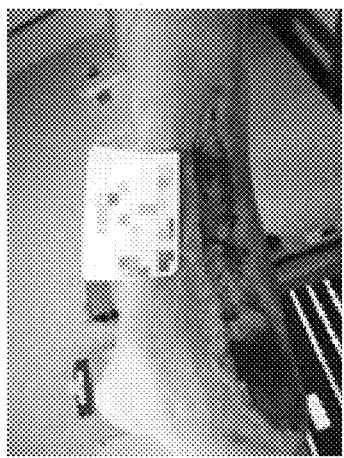
Figure 5D:
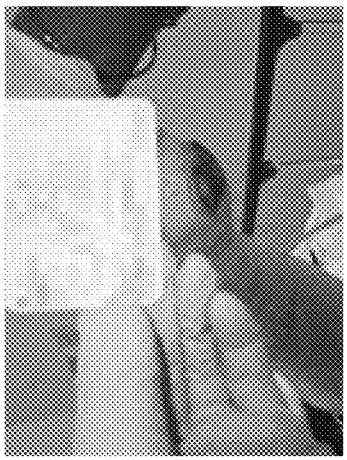
Figure 5A:
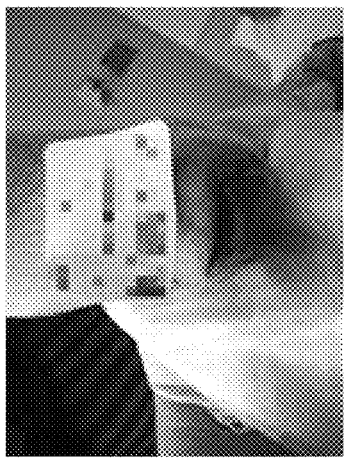

FIG. 4 illustrates an exemplary computer that can be used for making segmentation and automated measurements of chronic wound images. As used herein, "computer" may include a plurality of computers. The computers may include one or more hardware components such as, for example, a processor 421, a random access memory (RAM) module 422, a read-only memory (ROM) module 423, a storage 424, a database 425, one or more input/output (I/O) devices 426, and an interface 427. Alternatively and/or additionally, the computer may include one or more software components such as, for example, a computer-readable medium including computer executable instructions for performing a method associated with the exemplary embodiments. It is contemplated that one or more of the hardware components listed above may be implemented using software. For example, storage 424 may include a software partition associated with one or more other hardware components. It is understood that the components listed above are exemplary only and not intended to be limiting.

Processor 421 may include one or more processors, each configured to execute instructions and process data to perform one or more functions associated with a computer for discriminating tissue of a specimen. Processor 421 may be communicatively coupled to RAM 422, ROM 423, storage 424, database 425, I/O devices 426, and interface 427. Processor 421 may be configured to execute sequences of computer program instructions to perform various processes. The computer program instructions may be loaded into RAM 422 for execution by processor 421.

RAM 422 and ROM 423 may each include one or more devices for storing information associated with operation of processor 421. For example, ROM 423 may include a memory device configured to access and store information associated with the computer, including information for identifying, initializing, and monitoring the operation of one or more components and subsystems. RAM 422 may include a memory device for storing data associated with one or more operations of processor 421. For example, ROM 423 may load instructions into RAM 422 for execution by processor 421.

Storage 424 may include any type of mass storage device configured to store information that processor 421 may need to perform processes consistent with the disclosed embodiments. For example, storage 424 may include one or more magnetic and/or optical disk devices, such as hard drives, CD-ROMs, DVD-ROMs, or any other type of mass media device.

Database 425 may include one or more software and/or hardware components that cooperate to store, organize, sort, filter, and/or arrange data used by the computer and/or processor 421. For example, database 425 may store digital images of a wound, computer-executable instructions for determining at least one of a size, boundary or an area of the wound; and providing the determined at least one of the boundary, the size or the area of the wound, wherein the provided determined at least one of the size or the area of the wound is used to monitor wound healing. It is contemplated that database 325 may store additional and/or different information than that listed above.

I/O devices 426 may include one or more components configured to communicate information with a user associated with computer. For example, I/O devices may include a console with an integrated keyboard and mouse to allow a user to maintain a database of digital images, results of the analysis of the digital images, metrics, and the like. I/O devices 426 may also include a display including a graphical user interface (GUI) for outputting information on a monitor. I/O devices 426 may also include peripheral devices such as, for example, a printer for printing information associated with the computer, a user-accessible disk drive (e.g., a USB port, a floppy, CD-ROM, or DVD-ROM drive, etc.) to allow a user to input data stored on a portable media device, a microphone, a speaker system, or any other suitable type of interface device.

Interface 427 may include one or more components configured to transmit and receive data via a communication network, such as the Internet, a local area network, a workstation peer-to-peer network, a direct link network, a wireless network, or any other suitable communication platform. For example, interface 427 may include one or more modulators, demodulators, multiplexers, demultiplexers, network communication devices, wireless devices, antennas, modems, and any other type of device configured to enable data communication via a communication network.

EXAMPLES

The following examples are set forth below to illustrate the methods and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures and other reaction ranges and conditions that can be used to optimize the product purity and yield obtained from the described process.

Example 1—Wound Segmentation Based on a Probability Map

The wound images used in the disclosed experiments are provided by the Comprehensive Wound Center of the Ohio State University Wexner Medical Center, with Institutional Review Board (IRB) approval. The center is one of the largest wound centers in the US, and the wound images captured in the center comes from different camera manufacturers, setting and capture conditions: different medical center employees (not professional photographers) capturing the images in routine clinical work using different cameras. This simulates the variation that we expect to see in other medical centers in terms of patient variability as well as variation due to image capture. Unlike the wound images used in the literature, these images present additional challenges. As discussed in the previously herein, many previous works in this field are typically carried out in regions that contain the wound only, thus they do not have to deal with the issue of complicated background, especially those red, yellow and black objects, interfering with the segmentation process (see FIGS. 5A, 5B, 5C and 5D). In order to simplify the task at this stage, in some instances the algorithm requires the user to mark a single point (i.e. a single click) inside the wound to start the segmentation process.

Figure 6:
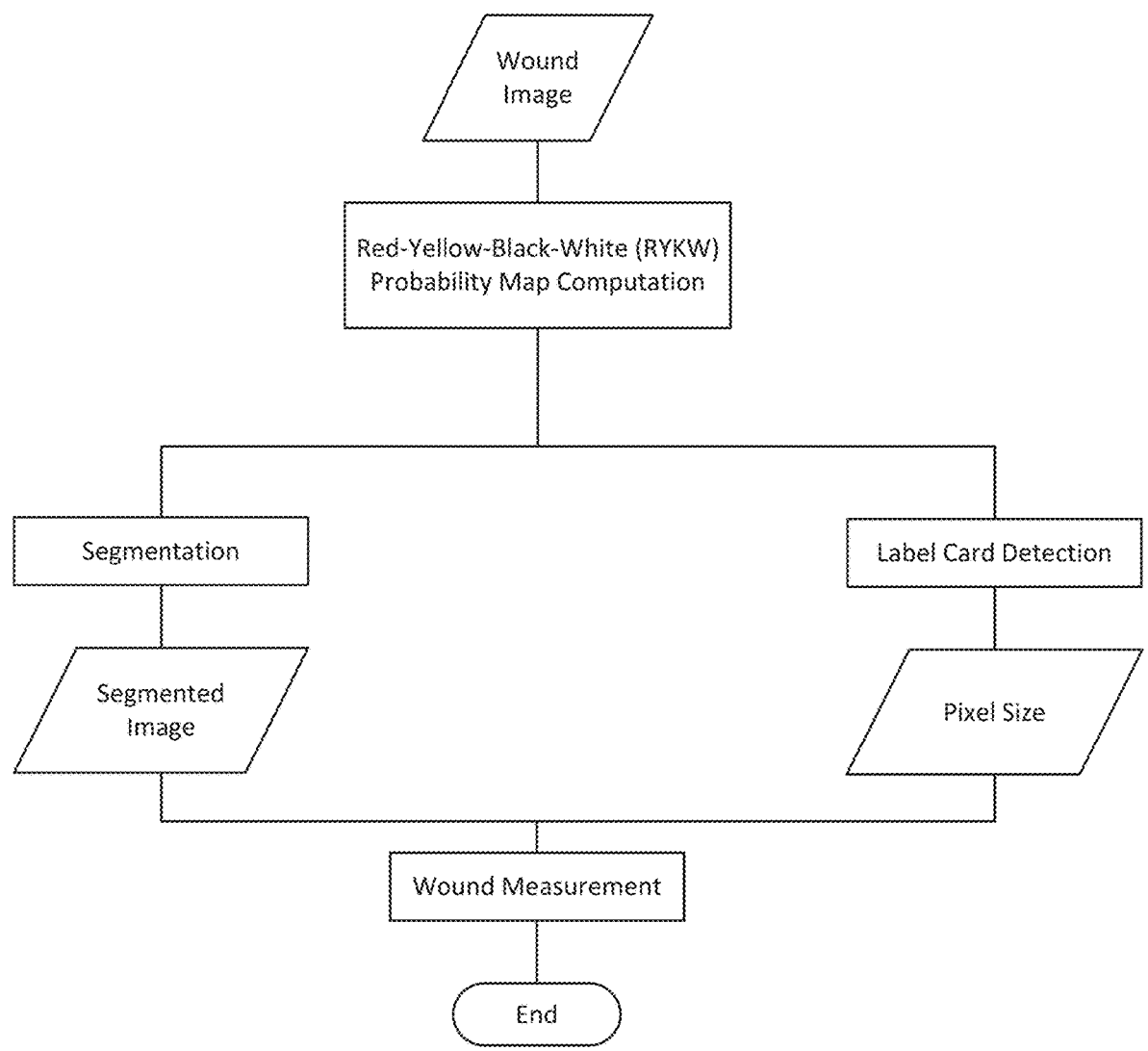
FIG. 6 is a flowchart that illustrates an exemplary method of for making segmentation and automated measurements of chronic wound images.

One of the disclosed methods comprises several stages as shown in FIG. 6. The first step is the red-yellow-black-white (RYKW) probability map computation in a modified HSV (Hue-Saturation-Value) color space. Once the probability map is established, the next step is the segmentation of the boundaries of the wound in the area. The results of two different segmentation approaches are presented: region growing segmentation and optimal thresholding. Because the distance between the camera and the wound is not recorded, this information needs to be extracted by the content in the image. One approach, which analyzes the image to detect patient labels typically attached near the wound, and uses the size of the label to calibrate the wound size measurements.

Probability Map Computation

Figure 7C:
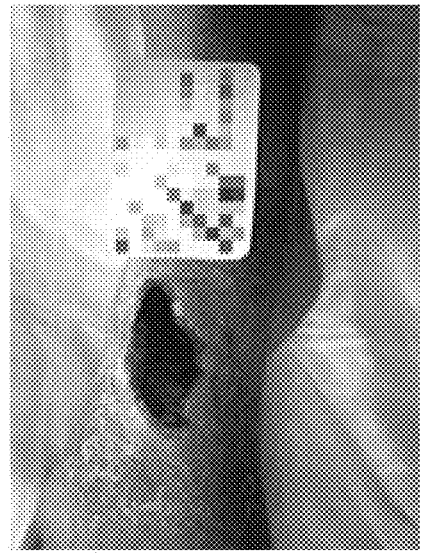
FIGS. 7A, 7B, AND 7C are photographs of wounds showing that granulation, slough and eschar tissues generally correspond to red (R), yellow (Y) and black (K) tissues, respectively in the wound area.
Figure 7B:
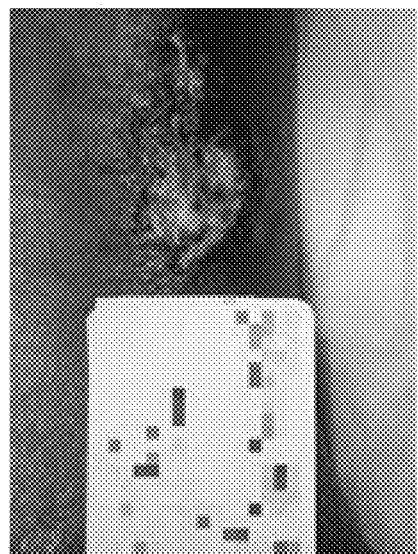
Figure 7A:
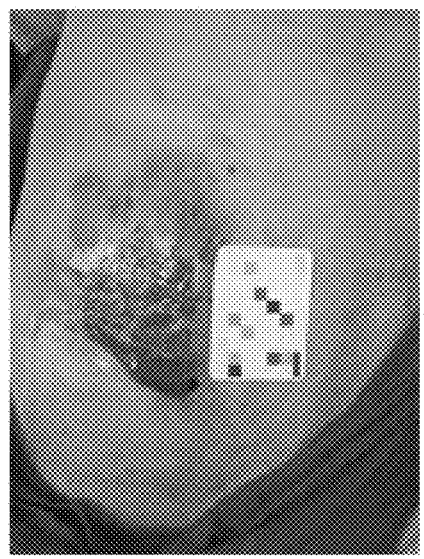

Granulation, slough and eschar tissues generally correspond to red (R), yellow (Y) and black (K) tissues, respectively in the wound area (see FIGS. 7A, 7B and 7C). Because subsequent stages requires the detection of white label cards, as well as to avoid any white pixels in the image being wrongly classified as yellow, a fourth color, white (W) is included in the probability map computation, resulting in a four-dimensional (4D) RYKW map. Given a wound image, the disclosed method computes the probability of each pixel in the image belonging to one of these colors. The probability is computed based on the distance of the image pixels to the red, yellow, black and white colors in a modified HSV color space. The HSV color space was chosen because it can be modified to maximize the distances between the four colors of interest (refer to Eq. 2 and Eq. 3, below).

Consider an image I, probability matrix P, and color set $C_k=\{R, Y, K, W\}$ where k=1, 2, 3, 4 represents the 4 colors R, Y, K, W respectively. For a particular pixel x within I, the probability p of the pixel belonging to a color $C_k$ (i.e. one of red, yellow, black or white) is computed through the following equation:

$$p_k(x) = \frac{1}{\left(\frac{d(C_k, x)}{d(R, x)}\right)^2 + \left(\frac{d(C_k, x)}{d(Y, x)}\right)^2 + \left(\frac{d(C_k, x)}{d(K, x)}\right)^2 + \left(\frac{d(C_k, x)}{d(W, x)}\right)^2} \quad (1)$$

where $d(C_k, x)$ is the distance (see Eq. 4-7) between the value of pixel x and the particular color $C_k$. In other words, the probability is inversely proportional to the relative distance between the pixel and the color of interest. The above equation is applied to all pixels for all four colors, producing a 4D probability map, P, with the sum of the probability at any one pixel is equal to 1. The probability definition used here is similar to that of the fuzzy c-means clustering method without the fuzzifier parameter. From the image point of view, the 4D matrix P can be viewed as a stack of 4 single matrices $P_k$, each showing the probability of the wound image pixels belonging to the 4 different colors. From the pixel point of view, the matrix P can be viewed as a collection of many vectors p, each showing the probability of individual pixels belonging to the 4 colors of interest.

Figure 8:
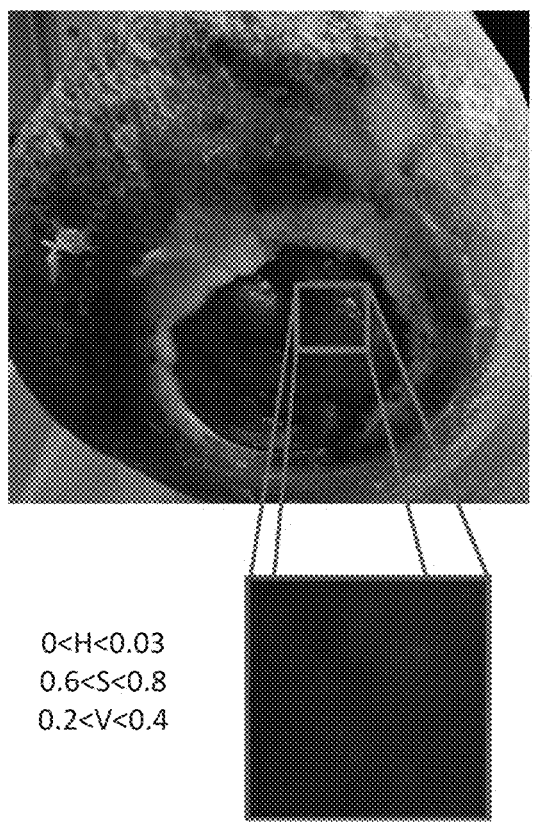
FIG. 8 is a photograph showing an example of a dark red granulation tissue whose Value channel, V, values range between 0.2 and 0.4.

One of the challenges in wound segmentation is to differentiate between regions with similar hue characteristics: e.g. dark red (granulation) vs. black (eschar) regions, as well as light yellow (slough) vs. white (epibole, skin etc.) regions. FIG. 8 shows an example of a dark red granulation tissue whose Value channel, V, values range between 0.2 and 0.4. Taking V=0.5 as the threshold, the tissue would have been misclassified as being closer to black rather than red (where 0 refers to pure black, and 1 refers to pure red). This, combined with the close proximity between red and yellow colors, makes segmentation of the three tissue types complicated, regardless of the color model used (RGB, HSV, CIE L*a*b* etc.). In this work, a modified HSV color model was developed to improve the accuracy of the probability map by scaling the Saturation (S) and Value (V) components according to Equations 2 and 3, respectively to obtain $S_{mod}$ and $V_{mod}$:

$$S_{mod} = \frac{\log(\alpha * S + 1)}{\log(\alpha + 1)} \quad (2)$$

$$V_{mod} = \frac{\log(\alpha * V + 1)}{\log(\alpha + 1)} \quad (3)$$

where $S_{mod}$ and $V_{mod}$ are the modified Saturation and modified Value respectively, and $\alpha$ is a constant. In our work, we have chosen $\alpha=8$ so that the first quarter of the original scale (dark or light regions) will be stretched to half the modified scale, while the remaining three quarters of the original scale (red or yellow regions) will be compressed to occupy the remaining half of the modified scale (see FIGS. 9A, 9B and 9C). Furthermore, the Hue (H) component is also shifted by 30° to maximize the distance between red and yellow.

Figure 9A:
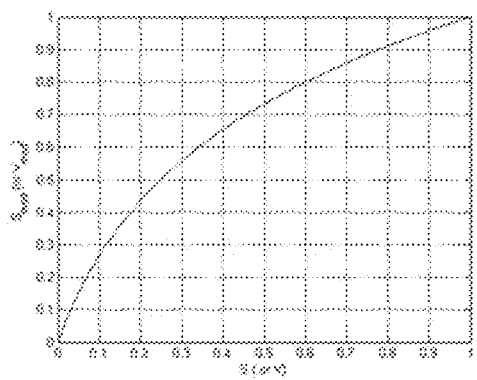
Figure 9B:
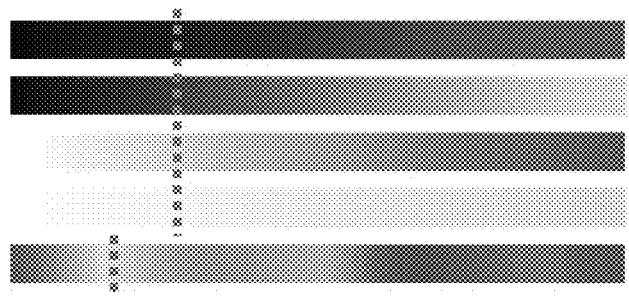
FIGS. 9B and 9C show the transformation of the black-red, black-yellow, white-red, white-yellow and red-yellow color transition from the standard HSV to the modified HSV color model.
Figure 9C:
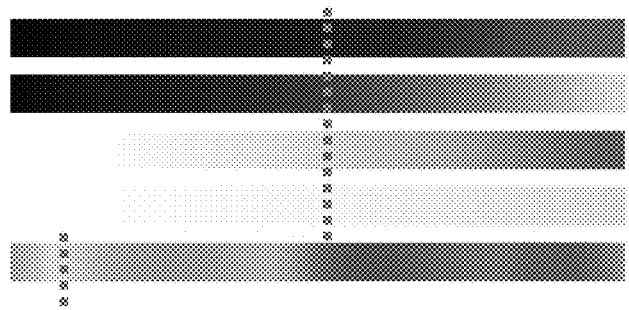

FIG. 9A shows the transformation of S and V using Eq. 2 and Eq. 3, while FIGS. 9B and 9C show the transformation of the black-red, black-yellow, white-red, white-yellow and red-yellow color transition from the standard HSV to the modified HSV color model. It can be observed that the modified HSV model better reflects the color distances between the four colors of interest. Under the standard HSV, dark red and dark yellow are closer to black; similarly, light red and light yellow are closer to white. This would negatively affect the accuracy of the color probability map. The proposed modified HSV model is thus better suited to computing the probability of pixels belonging to any one of the four colors (see below and Table XI for comparison between the modified and original HSV for region growing).

Due to the uneven color distribution of the HSV or modified HSV color models (e.g. dark colors occupied almost half of the entire color space), the calculation of distance, $d(C_k, x)$ between a particular pixel, x and the colors is defined differently for the four colors. The distance of a pixel to black is based solely on $V_{mod}$, while the distance to white is based on $V_{mod}$ and $S_{mod}$. The distances to red and yellow on the other hand make use of all $V_{mod}$, $S_{mod}$ and $H_{mod}$. For a particular pixel x, the proposed distance equations are summarized below:

$$d(R, x) = \sqrt{(H_{mod}(x) - H_{mod}(R))^2 + (S_{mod}(x) - S_{mod}(R))^2 + (V_{mod}(x) - V_{mod}(R))^2} \quad (4)$$

$$d(Y, x) = \sqrt{(H_{mod}(x) - H_{mod}(Y))^2 + (S_{mod}(x) - S_{mod}(Y))^2 + (V_{mod}(x) - V_{mod}(Y))^2} \quad (5)$$

$$d(K, x) = V_{mod}(x) - V_{mod}(K) \quad (6)$$

$$d(W, x) = \sqrt{(V_{mod}(x) - V_{mod}(W))^2 + (S_{mod}(x) - S_{mod}(W))^2} \quad (7)$$

where the following values are defined:

$V_{mod}(K)=0 V_{mod}(W)=1 S_{mod}(W)=0$ $H_{mod}(R)=11/12 S_{mod}(R)=1 V_{mod}(R)=1$ $H_{mod}(Y)=1/12 S_{mod}(Y)=1 V_{mod}(Y)=1$ Segmentation While there are many possible segmentation methods for use in medical applications, e.g., we based our segmentation on two well-known and rather basic techniques, namely region growing segmentation, and optimal thresholding. We will demonstrate that even with these two simple segmentation algorithms, when coupled with our proposed probability map approach, is able to provide reliable segmentation of wounds. While the proposed approach works with the selection of an initial seed point by a clinician, the RYKW map has the potential to improve the segmentation into fully automated segmentation. This can be achieved by first identifying all potential wound regions throughout the entire image based on color information, before carrying out advanced image analysis to filter the false positive regions, leaving only true wound regions as the segmented output.

Region Growing

Region growing is a pixel-based image segmentation algorithm that examines neighboring pixels of initial seed points and determines whether neighbors of the pixel should be added to the region. In our proposed method, the initial seed points are to be provided by the clinician. The regions are grown from the initial seed point's probability vector to adjacent points based on the 4D probability map P (Equation 1). A neighbor is added to the region if the distance between that pixel's probability vector and the mean probability vector of the region (i.e. the mean probability of each R, Y, K, W channel over the current segmented region) is less than a certain threshold value, t. The process continues until either all the neighbor's distances are above the threshold, or all the pixels have been processed.

To ensure the region growing process does not stop prematurely, a mechanism is included to search for pixels with a similar probability map within a certain radius, r, from the region boundary, and the process continues. Morphological closing and filling operations are then applied during post-processing to remove noise and soften the edges. From experiments, suitable values for the threshold and radius are t=0.1 and r=5 pixels, respectively. Note that the proposed algorithm only segments the granulation, slough and/or eschar regions and ignores the rest of the image as clinicians are only interested in the wounds. While region growing is generally considered as computationally expensive operation, the probability map really helps to speed up the process by providing a valuable color discriminator between the four colors of interest.

Optimal Thresholding

Our "optimal thresholding approach" segments the image by thresholding the difference matrix of the probability map, P, while taking into account the pixel's tissue type and strength of its probability. While there are many available thresholding methods such as Otsu thresholding that can be used to segment the probability map, these methods are rather "hard" thresholding methods; if single wounds are inadvertently separated to two or more smaller wounds (which can happen very frequently due to illumination etc.), the segmentation can be considered to fail since the calculated accuracy will be very low.

The idea behind the disclosed approach is first to identify all pixels whose color characteristics are similar to those of the seed pixel, before iteratively refining the segmentation boundary. The refinement is by simple thresholding of the difference matrix, Q, which is a matrix of the difference between the two highest probabilities for each pixel, and provides a second degree of tissue membership probability:

$$Q = P_{max1} - P_{max2} \quad (8)$$

where $P_{max1} = \max(P)$ and $P_{max2} = \max(P)|_{P \neq P_{max1}}$.

Given the seed point pixel and its probability vector, its highest probability tissue class is identified, and pixels with the following properties are considered for segmentation:

Property 1: Pixels with the same tissue class as their highest probability. Value of Q ranges from 0 to the maximum value in Q, $\varphi$.

Property 2: Pixels with the same tissue class as their second highest probability, and in which their difference with the highest probability is below a certain threshold, $\tau$. Value of Q ranges from 0 to $-\tau$.

In the strictest sense, only pixels with Property 1 should be included in the segmented region; however, due to the complicated nature of the wound tissue, pixels with Property 2 are also included to minimize false negative. The region of interest (ROI) at this point is defined as the region in Q whose pixels satisfy either Property 1 or Property 2, with values ranging between the $\varphi$ and $-\tau$.

The next step is to iteratively threshold the ROI, starting from $\varphi$. At each step the mean of the segmented ROI where the seed point is located is calculated. Theoretically the mean will decrease as the threshold value decreases towards $-\tau$. The optimal threshold is defined as the threshold value where the mean values become 'stable' without any sudden decreases or increase. The segmented wound region can then be obtained by thresholding the ROI with the optimal threshold value. As in the region growing, morphological closing and filling operations are then applied during post-processing to obtain the final segmentation. Experimentally, the suitable values for the threshold, $\tau$, and step size decrement, step, are $\Sigma=0.1$ and step=0.01, respectively. The whole process is summarized as pseudo-code in Table I.

TABLE I

PSEUDO-CODE OF THE OPTIMAL-

Input: 4D probability map, P
Output: Segmented wound region, $I_{seg}$
Procedure:
1. Compute probability difference matrix, Q
2. Based on probability map of seed pixel, identify ROI
3. Set $\varphi$ = max(Q)
4. Set $\tau$ = 0.1
5. Set step=0.01
6. Set th = $\varphi$
7. While th > $-\tau$
    seg = ROI > th
    segmean = mean(seg)
    th = th − step
  end
8. Identify optimal threshold, $th_{opt}$ based on segmean
9. $I_{seg}$ = ROI > $th_{opt}$ Label Card Detection and Wound Measurement Since the distance between the camera and the wound is not recorded, the absolute values for wound measurements—necessary for clinical reporting—cannot be recorded. To solve this problem, we have developed a technique to automatically scale the wound size. As in most medical centers, each of the wound images taken at the Wexner Medical Center contains a white label card, which we automatically detected and used as a reference to compute the actual pixel size in the image. The white label card has a standard size of 4.5 cm by 6.5 cm. With successful detection of the card and its size with respect to the image, we can easily calculate the pixel measurements in cm per pixel unit.

To detect the card, first the white regions are identified from the same RYKW map computed in the previous step. Then, the detected white regions are filtered based on their area, rectangularity (actual area over minimum bounding rectangle area) and convexity measure (actual area over convex hull area) to identify potential rectangular regions for the white card. The rectangularity and convexity measure helps in eliminating irregular shape region, while the area relative to the image size helps in eliminating false rectangular regions. The length and width of the identified label card are then used to calibrate the pixel size. With the pixel size available, measuring the wound size is straightforward. Currently, the proposed algorithm outputs three measurements: area, length (major diameter) and width (minor diameter) of the segmented wound.

Experimental Setup

This study was done with the institutional review board (IRB) approval. In our experiments, we used a total of 80 images, whose ground truth was provided by at least two clinicians. The images are of 768×1024 pixels in resolution, stored in JPEG format. They were captured by the clinicians following normal clinical practice and under non-controlled conditions, i.e. no measures were taken to control the illumination, background or the wound to background ratio, resulting in a very challenging set of images. To capture the ground truth, an in-house software tool was developed. Using this tool, clinicians can draw not only the boundaries of the wound but also its three tissue components: granulation, slough and eschar tissues. Again, using this tool, the user can input the estimates (as a percentage) for tissue components that are already an integral part of wound documentation. The clinicians first manually drew the wound boundaries for each image independently. Based on the drawn boundaries, the clinicians were then asked to estimate the percentage of granulation, slough and eschar tissues before proceeding to draw the boundaries for each tissue type. The tool is capable of handling as many number of wound or tissue regions possible, hence the clinicians were asked to provide as detail a drawing as possible. Depending on the complexity of the image, clinicians spent between 30 seconds to 3 minutes to annotate a single image.

TABLE II

CATEGORIZATION OF IMAGES

| Sets | Number of Images | Number of Ground Truth |
|---|---|---|
| Set 1 | 10 | 1 (consensus from 3 clinicians) |
| Set 2 | 15 | 3 (from 3 clinicians) |
| Set 3 | 55 | 2 (from 2 clinicians) |

The images were divided into three sets as shown in Table III. Set 1, consisting of 10 images, were annotated with the consensus of three clinicians, and used as a training set to ensure that all three clinicians have the same understanding in defining the different tissue types as well as their boundaries. Set 2, with 15 images, were annotated by all three clinicians separately, producing three separate ground truth files for each image. Finally Set 3, with 55 images, were annotated by two clinicians independently, resulting in two separate ground truth files. The wound and tissue boundaries from the ground truth files of Sets 2 and 3 are compared to evaluate the level of agreement between the clinicians. Tissue component percentage estimation by the clinicians were also compared to the actual tissue percentage from the drawings to evaluate the accuracy of the clinicians' estimation.

The inter-reader variability is measured using the agreement measure in Eq. 9:

$$\text{Agreement} = \frac{D_1 \cap D_2}{D_1 \cup D_2} \times 100 \quad (9)$$

where $D_1$ and $D_2$ refer to the region annotated by the first, second or third clinician, respectively. Due to the high degree of inter-reader variability (to be discussed in the Section V), it is difficult to obtain one common ground truth for Sets 2 and 3. Hence, to evaluate the accuracy of computer segmentation, the resulting segmentation is compared to each of the different ground truths. In other words, the segmentation results are compared to each clinician's manual drawings, thereby indicating with which proposed algorithm the clinicians tend to agree more.

The same measurement in Eq. 9 is used to determine the accuracy of the computer segmented regions against the ground truth:

$$\text{Accuracy} = \frac{GT \cap CS}{GT \cup CS} \times 100 \quad (10)$$

where GT refers to the boundaries drawn by any one of the clinicians, and CS refers to the computer segmented region.

Experimental Results and Discussion

We first present the inter-reader variability between clinicians on the wound boundaries, tissue characterization as well as tissue percentage estimation. The proceeding subsection will then report the results of the computer segmentation against all the ground truth discussed herein.

Inter-Reader Variability Between Clinicians

As explained herein, two clinicians independently drew the boundaries of the wounds in Set 2 as well as estimated the percentages of tissue types. In this section, this data will be used to evaluate inter-reader variability. Table III shows the statistics of wound boundary agreement between the clinicians for the images in Set 2. Since there are three clinicians involved, four sets of comparison are carried out. As can be observed from Table IV, the mean agreement between any two clinicians varies between 80.3-84.3%. The mean drops to 74.3% when all three clinicians' readings are compared, indicating that it is more difficult to reach an agreement when more clinicians involved (the trend for the median agreement follows a similar trend). Note that the minimum agreement goes as low as 40.7%, which suggests that some of the wounds are quite complicated and thus their boundaries are relatively difficult to define.

TABLE III

WOUND AGREEMENT FOR SET 2 IMAGES (PERCENTAGE ACCURACY MEASURE IN EQ. 9)

| Agreement Between | Mean | Min | Max | Med | Std Dev |
|---|---|---|---|---|---|
| Clinicians 1, 2 & 3 | 74.3 | 40.7 | 88.3 | 76.3 | 12.5 |
| Clinicians 1 & 2 | 84.3 | 69.7 | 94.4 | 86.1 | 7.4 |
| Clinicians 1 & 3 | 81.5 | 41.4 | 92.3 | 87.4 | 13.0 |
| Clinicians 2 & 3 | 80.3 | 55.0 | 92.7 | 83.2 | 10.5 |

TABLE IV

WOUND AGREEMENT FOR SET 3 IMAGES (PERCENTAGE ACCURACY MEASURE IN EQ. 9)

| Agreement Between | Mean | Min | Max | Med | Std Dev |
|---|---|---|---|---|---|
| Clinicians 2 & 3 | 67.4 | 24.5 | 94.5 | 70.8 | 19.5 |

Table IV shows the statistics for images in Set 3. Clearly, with more images, the mean and median agreement between clinicians 2 and 3 (clinician 1 is not involved in evaluating Set 3) drops rather sharply, from 80.3% to around 67.4% in mean agreement, and from 83.3% to 70.8% in median. The standard deviation also almost doubles, while the minimum agreement can be as low as 24.4%. This suggests that with increased number of images to annotate, some of which contain relatively complicated wounds, the agreement between the clinicians plummets. This is another reason why we will be comparing the computer segmentation with the ground truth from individual clinicians instead of a combined ground.

TABLE V

INTRA-READER VARIABILITY FOR WOUND AGREEMENT

| Agreement Between | Mean | Min | Max | Med | Std Dev |
|---|---|---|---|---|---|
| Clinicians 2 | 84.5 | 66.0 | 97.3 | 87.2 | 10.5 |
| Clinicians 3 | 80.4 | 58.0 | 97.3 | 84.8 | 14.7 |

TABLE VI

TISSUE AGREEMENT FOR SET 2 IMAGES

| Tissue Types | Agreement Between Clinicians | Mean | Min | Max | Med | Std Dev | # of Img |
|---|---|---|---|---|---|---|---|
| Granul | 1, 2&3 | 42.9 | 0.0 | 86.2 | 42.4 | 31.6 | 19 |
|  | 1&2 | 59.6 | 0.0 | 94.0 | 71.9 | 30.1 | 19 |
|  | 1&3 | 50.9 | 0.0 | 89.2 | 54.2 | 35.0 | 19 |
|  | 2&3 | 52.6 | 0.0 | 88.5 | 60.3 | 31.8 | 18 |
| Slough | 1, 2&3 | 17.8 | 0.0 | 63.1 | 0.2 | 24.3 | 15 |
|  | 1&2 | 31.3 | 0.0 | 74.2 | 27.0 | 31.7 | 13 |
|  | 1&3 | 29.1 | 0.0 | 72.7 | 17.7 | 31.2 | 14 |
|  | 2&3 | 38.4 | 0.0 | 84.7 | 44.8 | 33.4 | 15 |
| Eschar | 1, 2&3 | 24.5 | 0.0 | 85.8 | 0.0 | 37.7 | 9 |
|  | 1&2 | 37.4 | 0.0 | 90.5 | 0.0 | 46.7 | 7 |
|  | 1&3 | 26.5 | 0.0 | 90.8 | 0.0 | 40.8 | 9 |
|  | 2&3 | 48.5 | 0.0 | 91.4 | 55.4 | 34.4 | 8 |

TABLE VII

TISSUE AGREEMENT FOR SET 3 IMAGES

| Tissue Types | Agreement Between Clinicians | Mean | Min | Max | Med | Std Dev | # of Img |
|---|---|---|---|---|---|---|---|
| Granul | 2 & 3 | 42.7 | 0.0 | 93.9 | 51.1 | 34.6 | 65 |
| Slough | 2 & 3 | 15.9 | 0.0 | 90.1 | 0.0 | 27.3 | 42 |
| Eschar | 2 & 3 | 25.0 | 0.0 | 92.3 | 0.0 | 34.6 | 30 |

TABLE VIII

TISSUE PERCENTAGE ESTIMATION

| Sets | Clinicians | Mean | Min | Max | Med | Std Dev | # of Img |
|---|---|---|---|---|---|---|---|
| Set 2 | 1 | 23.3 | 7.6 | 51.7 | 19.4 | 12.8 | 14 |
|  | 2 | 22.8 | 1.2 | 73.2 | 19.3 | 20.4 | 18 |
|  | 3 | 19.5 | 0.7 | 48.4 | 16.4 | 14.8 | 16 |
| Set 3 | 2 | 28.8 | 0.2 | 160.0 | 18.6 | 31.0 | 46 |
|  | 3 | 25.4 | 0.1 | 132.7 | 16.3 | 27.4 | 53 |

To gauge intra-reader variability, we have also asked two of the clinicians to re-draw the wound boundary for a subset of cases (10 images) after a month from their initial reading. The intra-reader variability is summarized in Table V. As in the inter-reader variability (Table III), the difference between two consecutive readings is relatively high, with average self-agreement of 80.4% and 84.5% for the two clinicians.

Figure 10A:
FIGS. 10A and 10B show two examples of images with the lowest agreement between two clinicians.
Figure 10B:
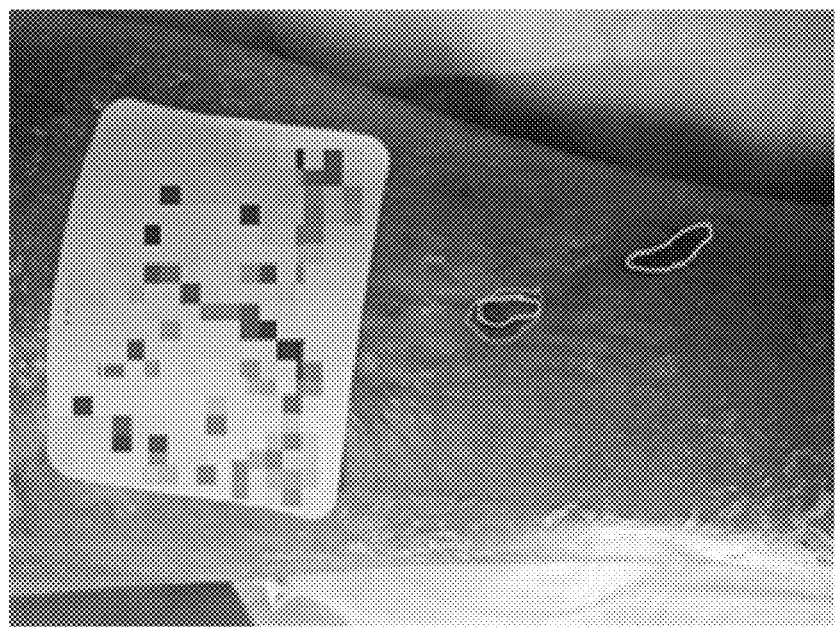
Figure 11A:
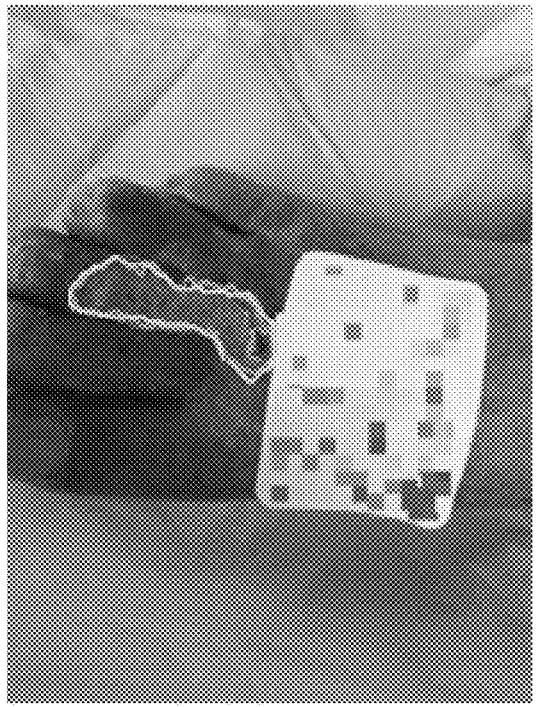
FIGS. 11A, 11B, 11C and 11D show four examples of the results obtained using both segmentation methods.
Figure 11B:
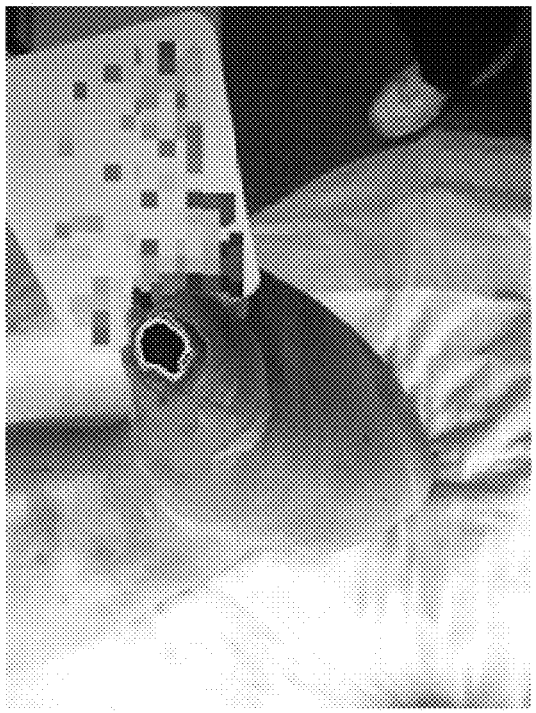
Figure 11C:
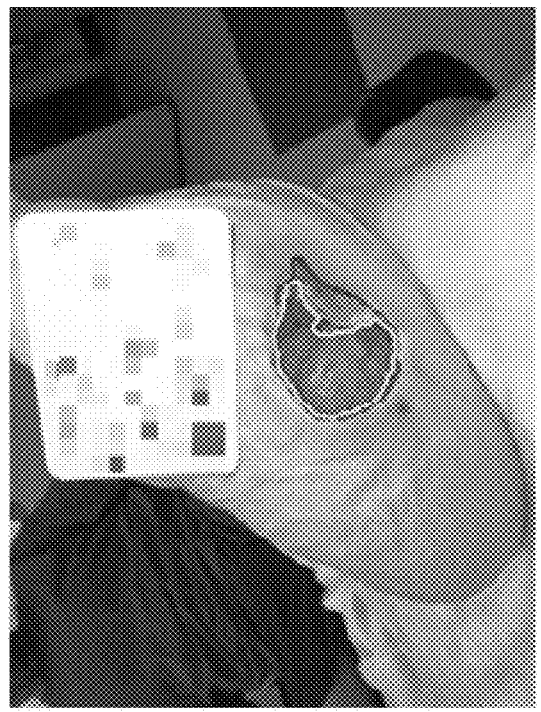
Figure 11D:

While the average agreement between the clinicians at the wound level may still acceptable, their agreement at the tissue level is much lower. Tables VI and VII show the tissue characterization agreement between the clinicians for Sets 2 and 3, respectively. It can be seen that the mean and median agreement are all below 60% with standard deviation of mostly more than 30%. There were many instances where the clinicians do not agree on the particular tissue types within the wound, especially when it comes to differentiating granulation and slough, or between slough and eschar, and even granulation and epithelium. This is the reason for minimum agreement (all the values in the 'Min' column in Tables VI and VII) to be 0%. In other words, there are always situations where one clinician will identify a particular region within the wound, with which the other clinician will not agree. For example, FIGS. 10A and 10B show two examples of images with the lowest agreement between two clinicians. While the clinicians show quite decent agreement when it comes to granulation, their agreement for slough and eschar tissues is very low. Again, as in determining agreement on wound boundaries, the more the number of clinicians involved (3 vs. 2), the lower the agreement. Similarly, the more the images (Set 3 vs Set 2), the lower the overall agreement is.

The last comparison we made regarding the clinicians ground truth is on the accuracy of their tissue percentage estimation. During annotation, once they completed drawing the overall wound boundaries for an image, the clinicians were asked to estimate the percentage of granulation, slough and eschar tissues within the wound boundaries. They were then required to draw the tissue boundaries within the wound, and these 'actual' percentages were compared to their earlier estimates. Wounds with only one tissue type (e.g. granulation only) were excluded as for these images they were not required to estimate (automatically set to 100%). Table VIII shows the percentage differences for the three clinicians for Set 2 and Set 3. The values are computed as the absolute difference between all three tissue types (hence some differences exceed 100%). As an example, a computer calculated percentages of (60% granulation, 20% slough and 20% eschar) against clinician's estimation of (80% granulation, 10% slough and 10% eschar) will give an error rate of 40%: 20% error from the granulation, and 10% error each from the slough and eschar. It can be seen that the mean differences between the three clinicians are almost the same, which are around 20% for Set 2, and around 25% for Set 3. This suggests that even the most experienced of clinicians are having trouble estimating the tissue percentages, which is an important piece of information required in wound documentation.

The results presented in this section show that wound segmentation and characterization are complicated processes, where even the most experienced clinicians have different opinions regarding wound boundaries and the type of tissues involved. The next section will discuss the results of the computer segmentation, and we will demonstrate that the proposed segmentation algorithm based on a probability map can be as good as the clinicians' consensus ground truth.

Segmentation and Measurement Accuracy

We carried out both qualitative and quantitative evaluations of the algorithm performance and these results will be presented in the next two subsections.

Qualitative Evaluation

First, the performance of the segmentation algorithm was evaluated qualitatively. FIGS. 11A, 11B, 11C and 11D show four examples of the results obtained using both segmentation methods. For the first case (FIG. 11A, granulation), the accuracy is 91.3% and 77.7% compared to the ground truth by Clinicians 2 and 3, respectively using the optimal thresholding, and 83.6% and 71.2% using the region growing segmentation. The discrepancies between the results against the different ground truths are caused by the rather big difference in the wound boundaries created by the two clinicians. For the second case (FIG. 11B, granulation), the accuracies for both segmentation methods against both clinicians' ground truths are all more than 90%.

For the third example (FIG. 11C, eschar), the accuracies are all more than 80% except for the optimal thresholding result against Clinician 3, which is around 75%. Finally, for case 4 (FIG. 11D, eschar), the accuracies for the optimal thresholding are recorded as 58.6% and 86.3%, while the region growing scores were 39.4% and 62.2%. As in case 1, the two clinicians differed in defining the wound boundary, where one of them included some parts of healed tissues as well, lowering the accuracy percentages for both methods. The optimal thresholding method agrees well with Clinician 3 with 86.3% accuracy, although the region growing approach seems to have missed some boundary pixels. The small size of the wound also contributes to further lower the accuracy of this particular wound image, due to the 'unforgiving' measurement metric used. Nevertheless, the four examples demonstrate that despite the complex nature of the wound boundary, the proposed algorithm is able to segment the wounds rather accurately.

Quantitative Evaluation

Tables IX and X present the overall segmentation accuracy using optimal thresholding and region growing approach respectively. Each table presents the results according to the different image sets as well as different clinicians' ground truths. It is observed that using optimal thresholding segmentation on the probability map provides slightly better overall results compared to using region growing. However, these differences diminish as the size of the dataset increases (i.e. Set 1→Set 3), and the average accuracies become almost identical (74.0% vs 74.2%). This trend is also true for individual clinician's agreements with the algorithm for different methods. Optimal thresholding is also more consistent than region growing as can be deduced by the lower standard deviation for all image sets. The overall average accuracy of 75% is very promising considering the level of agreement between the clinicians varies from 65% to 85%.

We also compare the performance of our method with the one proposed by Kolesnik and Fexa, summarized in Table XI. Their method, like ours and unlike the other works discussed in Section II, is not limited to images captured under controlled environment, not confined to the wound region, or designed for specific wound types only. Furthermore, besides supervised automatic mode, their method can also work on semi-automatic mode by requiring the user to provide samples of pixels belonging to wound and non-wound regions. These two factors make the Kolesnik and Fexa method, which is based on color and texture features with SVM classifier, the most appropriate benchmark for our proposed method. Comparing the readings in Table IX, X and XI, both of our approaches outperform the Kolesnik and Fexa method, which only records 68.8% average accuracy. Based on the standard deviation readings, we can also deduce that our approach is more consistent. This is expected as Kolesnik and Fexa's approach depends heavily on the pixel samples to start the segmentation. While our approach requires the user to provide only an initial seed (i.e. a single clickon an image), which is more convenient for the clinicians, the other method requires two sets of samples.

TABLE IX

AVERAGE SEGMENTATION (%) RESULTS FOR OPTIMAL THRESHOLDING

| Sets | Consensus | Clinician 1 | Clinician 2 | Clinician 3 | Average | Std. Dev. |
|---|---|---|---|---|---|---|
| Set 1 | 78.6 | NA | NA | NA | 78.6 | 8.0 |
| Set 2 | NA | 79.6 | 77.4 | 73.5 | 76.8 | 9.8 |
| Set 3 | NA | NA | 74.8 | 73.2 | 74.0 | 10.8 |
| Overall | 78.6 | 79.6 | 75.4 | 73.3 | 75.1 | 10.5 |

TABLE X

AVERAGE SEGMENTATION (%) RESULTS FOR REGION GROWING

| Sets | Consensus | Clinician 1 | Clinician 2 | Clinician 3 | Average | Std. Dev. |
|---|---|---|---|---|---|---|
| Set 1 | 70.8 | NA | NA | NA | 70.8 | 14.3 |
| Set 2 | NA | 77.1 | 75.7 | 73.6 | 75.4 | 10.8 |
| Set 3 | NA | NA | 74.3 | 74.0 | 74.2 | 12.0 |
| Overall | 70.8 | 77.1 | 74.6 | 73.9 | 74.0 | 13.1 |

TABLE XI

AVERAGE SEGMENTATION (%) RESULTS FOR KOLESNIK & FEXA METHOD

| Sets | Consensus | Clinician 1 | Clinician 2 | Clinician 3 | Average | Std. Dev. |
|---|---|---|---|---|---|---|
| Set 1 | 65.1 | NA | NA | NA | 65.1 | 22.8 |
| Set 2 | NA | 78.9 | 78.3 | 80.4 | 79.2 | 10.4 |
| Set 3 | NA | NA | 66.7 | 66.7 | 66.7 | 17.3 |
| Overall | 65.1 | 78.9 | 69.2 | 69.6 | 68.8 | 17.0 |

TABLE XII

AVERAGE SEGMENTATION (%) RESULTS ACCORDING TO TISSUE TYPES

| Tissues | Optimal Threshold | Region Growing |
|---|---|---|
| Granulation | 76.2 | 75.3 |
| Slough | 63.3 | 63.9 |
| Eschar | 75.1 | 71.5 |

TABLE XIII

PERFORMANCE COMPARISON (%) BETWEEN MODIFIED AND ORIGINAL HSV FOR REGION GROWING

| Tissues | Modified HSV | Original HSV |
|---|---|---|
| Overall | 74.0 | 62.9 |
| Granulation | 75.3 | 58.9 |
| Slough | 63.9 | 57.2 |
| Eschar | 71.5 | 66.8 |

Table XII shows the segmentation accuracy according to the different tissue types. Both approaches work best in segmenting granulation and eschar tissues, with lower accuracy for slough tissue. This is not surprising given the better delineated boundaries of granulation and eschar tissues. Slough tissues appear more sporadic, and also may be easily confused with other tissue types. This finding also agrees with the one reported by Wannous et. al. Table XIII compares the segmentation accuracies of the region growing approach between the proposed modified HSV color space and the original HSV color space. Clearly, without modifying the HSV color space, the segmentation performance decreases considerably; highlighting the importance of our proposed modification. Without the modification, each of the overall wound segmentation as well as the granulation, slough and eschar tissues segmentation recorded a drop in accuracy between 5% to 15%. As expected, the granulation tissue segmentation benefits the most from our modified color space because better threshold is used to distinguish dark red (granulation) and black (eschar) tissues.

Optimal thresholding has much lower computational complexity compared to the region growing method. Region growing processes all the wound pixels, hence, the larger the image or the wound, the longer time is needed to complete processing all the pixels of interest. On average, to segment an image of size 768×1024 on 2.3 GHz Intel® Core™ i7 processor, optimal thresholding needed less than a second, while region growing required up to five seconds, depending on the wound size. Another issue to be considered when using the region growing approach for segmentation is the repeatability, i.e. the method should provide consistent segmentation results for different initial seeds. This is particularly even more challenging in our case as wound images tend to have "glossy" pixels within the granulation or slough area due to their wet nature. The optimal thresholding segmentation does not suffer from this problem, and thus is relatively more stable. Nevertheless, the proposed probability map approach, together with the mechanism to prevent premature stopping, is able to address this issue rather well.

CONCLUSION

We have developed a method for the segmentation of wound images into granulation, slough and eschar regions and automatically carry out the measurements necessary for wound documentation. We propose the red-yellow-black-white (RYKW) probability map as the platform for the region growing process in segmenting the three regions as well as the white label cards. Experiments were conducted on 80 wound images provided by The Ohio State University Wexner Medical Center. These images exhibited challenging characteristics with different types of wounds at different stages, typically pictured in a clinical setting with complicated backgrounds, some of which with similar characteristics to the color palette of the wounds or surrounding healthy skin. The analysis presented from the inter-reader variability experiment suggests that wound segmentation and characterization are a complicated process, where even the most experienced clinicians have different opinions regarding wound boundaries and the type of tissues involved.

Using the optimal thresholding approach, the proposed method achieves an overall accuracy of 75.1%, which is very promising considering that the average agreement between the clinicians is between 67.4 to 84.3%. The wound area, length and width measurements also give a promising accuracy of 75.0%, 87.0% and 85.0%, respectively. We have also demonstrated that the probability map approach, computed through a modified HSV color model, is a very promising method for use with many segmentation techniques to reliably segment wound images. Based on two simple segmentation methods, optimal thresholding and region growing, the overall accuracy of around 75.1% has been observed. This suggests that the proposed RYKW map manages to identify the wound and its different tissues rather well, on par with the experts. Utilizing the RYKW map with a more advanced segmentation method can only further improve the accuracy of the segmentation, and is currently being worked on in our lab.

It should be noted that the quality of the segmentation results as well as the resulting measurements depend on the quality of the input images. Unlike most of the previous work in this area, our work aimed at developing a solution that will work with actual, clinically captured images (all the images in this study were captured during routine clinical work and the personnel who captured them were not aware of software development). However, there is still the expectation that the images capture the wound in a reasonable manner; for example, if only a tiny portion of the wound is visible in the image, obviously, the segmentation will fail to properly capture the wound or its tissue components. Admittedly, human readers will run into the same challenge if asked to evaluate such images. Similarly, if the labels are not placed reasonably well, the absolute measurements may be skewed. Although our software can recognize some of the variations in the placements of cards, it cannot recover from severely distorted placement of cards. A ruler and color scale in the label cards can be easily included and these can be used to calibrate both size measurements and color variations, hence improving the overall accuracy. Other image acquisition issues include poor lighting and noise. While some of the images in our dataset do suffer from non-uniform lighting, noise and/or other artifacts (e.g. blurring in the images due to shaking the camera while taking the picture) to a certain degree, the proposed method performs rather well in handling these types of images. A future study needs to analyze the effect of such variations on the overall performance in a controlled manner.

The proposed algorithm has some limitations in segmenting and characterizing wounds on dark skins, especially when trying to identify eschar tissues or dark granulation tissues. In some rare instances, the color of Caucasian skins tend to be very red in appearance (in which the probability of red will be very high), hence segmenting fresh granulation tissues may not work on these images. We are exploring the possibility of incorporating edge and depth analysis into the current algorithm in order to address these problems, which could also potentially measure undermining wounds. In addition, work is currently under way to further improve the segmentation accuracy by applying other segmentation techniques on the probability map. Automatic detection of the wounds, which would eliminate the need for the seed pixel by the user, is also under consideration. The proposed RYKW map is conveniently suited to achieve this by first identifying potential wound region throughout the entire image based on color information, before carrying out advanced analysis to filter the false positive regions. Finally, the ultimate goal of the wound software is not only to be able to characterize the wound at a single time, but also at multiple time periods. By comparing the wound characteristics from the first visit to the second and subsequent visits, as well as taking into account the demographic information of the patient (age group, gender, ethnicity) and the type of ulcers (diabetic, venous, pressure), the healing rate can be estimated. This would be a significant breakthrough in wound healing management.

While the methods and systems have been described in connection with preferred embodiments and specific examples, it is not intended that the scope be limited to the particular embodiments set forth, as the embodiments herein are intended in all respects to be illustrative rather than restrictive.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification.

Throughout this application, various publications may be referenced. The disclosures of these publications in their entireties are hereby incorporated by reference into this application in order to more fully describe the state of the art to which the methods and systems pertain.

It will be apparent to those skilled in the art that various modifications and variations can be made without departing from the scope or spirit. Other embodiments will be apparent to those skilled in the art from consideration of the specification and practice disclosed herein. It is intended that the specification and examples be considered as exemplary only, with a true scope and spirit being indicated by the following claims.

The invention claimed is:

1. A method for segmentation and automated measurement of chronic wound images using a smartphone, said method comprising:
   obtaining a digital image of a wound using a camera of the smartphone;
   automatically determining from the digital image of the wound a boundary of the wound using a processor of the smartphone;
   automatically determining an area of the wound from the boundary of the wound using the processor of the smartphone by segmenting pixels of the digital image as belonging to the wound or not being associated with the wound;
   automatically transforming each of the one or more pixels segmented as belonging to the wound to a modified Hue-Saturation-Value (HSV) color space; and
   automatically classifying each of the one or more pixels segmented as belonging to the wound and transformed to the HSV color space as belonging to one of a tissue group comprised of granulation, slough or eschar tissue based on a distance of each of the one or more pixels segmented and transformed to red, yellow, black and white colors in the modified HSV color space using the processor of the smartphone.

2. The method of claim 1, further comprising automatically determining by the processor of the smartphone an area of at least one of the tissue groups that comprise the wound.

3. The method of claim 2, further comprising monitoring wound healing by comparing by the processor of the smartphone at least one of the area of the wound or the area of the at least one of the one or more tissue groups that comprise the wound to previously measured area of the wound or previously measured area of the at least one of the one or more tissue groups that comprise the wound to determine if the wound or the tissue group is changing in area.

4. The method of claim 1, wherein automatically determining the area of the wound using the processor of the smartphone comprises determining a pixel size for at least the one or more pixels of the digital image that are segmented as belonging to the wound.

5. The method of claim 4, wherein the pixel size is determined by placing an object of a known size proximate to the wound prior to capturing the digital image of the wound using the camera of the smartphone.

6. The method of claim 5, wherein determining the pixel size comprises the processor of the smartphone:
   detecting the object in the digital image using one or more image analysis algorithms;
   measuring a number of pixels that span a given detected edge of the object having the known size; and
   determining the pixel size by dividing the known size of the given detected edge by the number of pixels that span the given detected edge of the object.

7. The method of claim 1, wherein each of the one or more pixels segmented as belonging to the wound are transformed to the modified HSV color space by scaling Saturation (S) and Value (V) components of a HSV color space by:

$$S_{mod} = \frac{\log(\alpha * S + 1)}{\log(a + 1)} \text{ and}$$

$$V_{mod} = \frac{\log(\alpha * V + 1)}{\log(a + 1)},$$

where $S_{mod}$ and $V_{mod}$ are modified Saturation and modified Value of the modified HSV color space, respectively, and a is a constant.

8. The method of claim 1, wherein each of the one or more pixels segmented as belonging to the wound having the highest probability of being red are classified using the processor of the smartphone as granulation tissue, pixels having the highest probability of being yellow are classified using the processor of the smartphone as slough tissue, and pixels having the highest probability of being black are classified using the processor of the smartphone as eschar tissue.

9. The method of claim 1, wherein each of the one or more pixels segmented as belonging to the wound having the highest probability of being white are classified using the processor of the smartphone as epibole tissue, normal skin or an object of a known size in the digital image used to determine pixel size.

10. The method of claim 1, wherein at least some of the one or more pixels segmented as belonging to the wound are further identified as granulation, slough or eschar tissue based on a region-growing algorithm or an optimal thresholding algorithm using the processor of the smartphone.

11. The method of claim 1, further comprising the processor of the smartphone determining the boundary of the wound as an ordered vector of pixel coordinates.

12. The method of claim 11, wherein the boundary of the wound is displayed on a display of the smartphone as an overlay on the digital image with a color that's distinguishable from both the wound and surrounding tissue.

13. The method of claim 1, wherein determining the area of a wound comprises the processor of the smartphone:
   determining a maximum distance between two boundary pixel values;
   reporting the maximum distance as a length of the wound;
   determining a perpendicular maximum distance between two boundary pixels, wherein the perpendicular maximum distance is a maximum distance between two boundary pixels such that a straight line drawn between the two boundary pixels that form the perpendicular maximum distance would be perpendicular to a straight line drawn between the two boundary pixels that form the length of the wound;

reporting the perpendicular maximum distance as a width of the wound;

calculating pixel values of pixels that belong to the wound that are within the boundary of the wound; and reporting the total pixel values within the wound boundary as the area of the wound.

14. The method of claim 1, further comprising filtering false positive regions from the digital image.

15. A system for segmentation and automated measurement of chronic wound images comprising:

a smartphone, wherein the smartphone comprises an image capture device;

a memory; and a processor in communication with the memory, wherein the processor executes computer-readable instructions stored in the memory that cause the processor to;

obtain a digital image that has been captured by the image capture device, wherein at least a portion of the image comprises a wound;

automatically determine from the digital image of the wound a boundary of the wound using a processor of the smartphone; and automatically determine an area of the wound from the boundary of the wound using the processor of the smartphone by segmenting pixels of the digital image as belonging to the wound or not being associated with the wound;

automatically transform each of the one or more pixels segmented as belonging to the wound to a modified Hue-Saturation-Value (HSV) color space; and automatically classify each of the one or more pixels segmented as belonging to the wound and transformed to the HSV color space as belonging to one of a tissue group comprised of granulation, slough or eschar tissue based on a distance of each of the one or more pixels segmented and transformed to red, yellow, black and white colors in the modified HSV color space using the processor of the smartphone.

16. The system of claim 15, further comprising automatically determining by the processor of the smartphone executing computer-readable instructions stored in the memory an area of at least one of the tissue groups that comprise the wound.

17. The system of claim 16, further comprising the processor of the smartphone executing computer-readable instructions stored in the memory to compare at least one of the area of the wound or the area of the at least one of the one or more tissue groups that comprise the wound to previously measured area of the wound or previously measured area of the at least one of the one or more tissue groups that comprise the wound, said previously measured area of the wound or previously measured area of the at least one of the one or more tissue groups stored in the memory of the smartphone, to determine if the wound or the tissue group is changing in area, which is used to monitor wound healing.

18. The system of claim 15, wherein automatically determining the area of the wound using the processor of the smartphone comprises the processor executing computer-readable instructions stored in the memory to determine a pixel size for at least the one or more pixels of the digital image that are segmented as belonging to the wound.

19. The system of claim 18, wherein the pixel size is determined by placing an object of a known size proximate to the wound prior to capturing the digital image of the wound using the camera of the smartphone.

20. The system of claim 19, wherein determining the pixel size comprises the processor of the smartphone executing computer-readable instructions stored in the memory to:

detect the object in the digital image using one or more image analysis algorithms;

measure a number of pixels that span a given detected edge of the object having the known size; and determine the pixel size by dividing the known size of the given detected edge by the number of pixels that span the given detected edge of the object.

21. The system of claim 15, wherein each of the one or more pixels segmented as belonging to the wound are transformed to the modified HSV color space by scaling Saturation (S) and Value (V) components of a HSV color space by:

$$S_{mod} = \frac{\log(\alpha * S + 1)}{\log(a + 1)} \text{ and}$$

$$V_{mod} = \frac{\log(\alpha * V + 1)}{\log(a + 1)},$$

where and $S_{mod}$ and $V_{mod}$ are modified Saturation and modified Value of the modified HSV color space, respectively, and a: is a constant.

22. The system of claim 15, wherein pixels having the highest probability of being red are classified using the processor of the smartphone executing computer-readable instructions stored in the memory as granulation tissue, pixels having the highest probability of being yellow are classified using the processor of the smartphone executing computer-readable instructions stored in the memory as slough tissue, and pixels having the highest probability of being black are classified using the processor of the smartphone executing computer-readable instructions stored in the memory as eschar tissue.

23. The system of claim 15, wherein pixels having the highest probability of being white are classified using the processor of the smartphone executing computer-readable instructions stored in the memory as epibole tissue, normal skin or an object of a known size in the digital image used to determine pixel size.

24. The system of claim 15, wherein at least some of the pixels segmented as belonging to the wound are further identified as granulation, slough or eschar tissue based on a region-growing algorithm or an optimal thresholding algorithm using the processor of the smartphone executing computer-readable instructions stored thereon.

25. The system of claim 15, further comprising the processor of the smartphone executing computer-readable instructions stored in the memory to determine the boundary of the wound as an ordered vector of pixel coordinates.

26. The system of claim 25, wherein the processor executes computer-readable instructions stored in the memory to display the boundary of the wound on a display of the smartphone as an overlay on the digital image with a color that's distinguishable from both the wound and surrounding tissue.

27. The system of claim 15, wherein determining the area of a wound comprises the processor of the smartphone executing computer-readable instructions stored in the memory to:

determine a maximum distance between two boundary pixel values;

report the maximum distance as a length of the wound;

determine a perpendicular maximum distance between two boundary pixels, wherein the perpendicular maximum distance is a maximum distance between two boundary pixels such that a straight line drawn between the two boundary pixels that form the perpendicular maximum distance would be perpendicular to a straight line drawn between the two boundary pixels that form the length of the wound;

report the perpendicular maximum distance as a width of the wound;

calculate pixel values of pixels that belong to the wound that are within the boundary of the wound; and report the total pixel values within the wound boundary as the area of the wound.

28. The system of claim 15, further comprising the processor of the smartphone executing computer-readable instructions stored in the memory for filtering false positive regions from the digital image.

* * * * *